US011111546B2

(12) United States Patent
Parr et al.

(10) Patent No.: US 11,111,546 B2
(45) Date of Patent: *Sep. 7, 2021

(54) 3.4 KB MITOCHONDRIAL DNA DELETION FOR USE IN THE DETECTION OF CANCER

(71) Applicant: MDNA Life Sciences Inc., Wilmington, DE (US)

(72) Inventors: Ryan L. Parr, Thunder Bay (CA); Robert Thayer, Thunder Bay (CA); Gabriel D. Dakubo, Thunder Bay (CA); Jennifer Creed, Broomfield, CO (US); Kerry Robinson, Thunder Bay (CA); Andrea Maggrah, Thunder Bay (CA); Brian Reguly, Thunder Bay (CA)

(73) Assignee: MDNA Life Sciences, Inc., Wilmington, DE (US)

( * ) Notice: Subject to any disclaimer, the term of this patent is extended or adjusted under 35 U.S.C. 154(b) by 136 days.

This patent is subject to a terminal disclaimer.

(21) Appl. No.: 16/429,739

(22) Filed: Jun. 3, 2019

(65) Prior Publication Data
US 2019/0323087 A1 Oct. 24, 2019

Related U.S. Application Data

(63) Continuation of application No. 15/470,175, filed on Mar. 27, 2017, now Pat. No. 10,308,987, which is a continuation of application No. 14/874,155, filed on Oct. 2, 2015, now abandoned, which is a continuation of application No. 14/507,027, filed on Oct. 6, 2014, now abandoned, which is a continuation of application No. 12/748,120, filed on Mar. 26, 2010, now abandoned, which is a continuation-in-part of application No. 11/975,390, filed on Oct. 18, 2007, now Pat. No. 8,008,008, which is a continuation of application No. PCT/CA2006/000652, filed on Apr. 18, 2006, application No. 16/429,739, which is a continuation of application No. 15/470,175, filed on Mar. 27, 2017, now Pat. No. 10,308,987, which is a continuation of application No. 14/874,155, filed on Oct. 2, 2015, now abandoned, which is a continuation of application No. 14/507,027, filed on Oct. 6, 2014, now abandoned, which is a continuation of application No. 12/748,120, filed on Mar. 26, 2010, now abandoned, which is a continuation of application No. PCT/CA2007/001711, filed on Sep. 26, 2007.

(60) Provisional application No. 60/789,872, filed on Apr. 7, 2006, provisional application No. 60/721,522, filed on Sep. 29, 2005, provisional application No. 60/672,016, filed on Apr. 18, 2005.

(51) Int. Cl.
C12Q 1/6886 (2018.01)
C12Q 1/686 (2018.01)
G01N 33/574 (2006.01)

(52) U.S. Cl.
CPC ........... *C12Q 1/6886* (2013.01); *C12Q 1/686* (2013.01); *G01N 33/57415* (2013.01); *G01N 33/57434* (2013.01); *C12Q 2600/112* (2013.01); *C12Q 2600/118* (2013.01); *C12Q 2600/156* (2013.01)

(58) Field of Classification Search
None
See application file for complete search history.

(56) References Cited

U.S. PATENT DOCUMENTS

| 3,817,837 | A | 6/1974 | Rubenstein et al. |
| 3,850,752 | A | 11/1974 | Schuurs et al. |
| 3,939,350 | A | 2/1976 | Kronick et al. |
| 3,996,345 | A | 12/1976 | Ullman et al. |
| 4,275,149 | A | 6/1981 | Litman et al. |
| 4,277,437 | A | 7/1981 | Maggio |
| 4,366,241 | A | 12/1982 | Tom et al. |
| 5,565,323 | A | 10/1996 | Parker et al. |
| 6,344,322 | B1 | 2/2002 | Polyak et al. |
| 8,008,008 | B2 * | 8/2011 | Parr .................. A61P 35/00 435/6.12 |
| 10,308,987 | B2 * | 6/2019 | Parr .................. C12Q 1/6886 |
| 2002/0155438 | A1 | 10/2002 | Simpson et al. |
| 2003/0092019 | A1 | 5/2003 | Meyer et al. |
| 2004/0191769 | A1 | 9/2004 | Marino et al. |
| 2005/0026167 | A1 | 2/2005 | Birch-Machin et al. |
| 2005/0244851 | A1 | 11/2005 | Blume et al. |

FOREIGN PATENT DOCUMENTS

| CA | 2356536 | 2/2003 |
| EP | 0812922 | 12/1997 |

(Continued)

OTHER PUBLICATIONS

Ahern, The Scientist 9 (15), 20 (1995).*

(Continued)

*Primary Examiner* — Ethan C Whisenant
(74) *Attorney, Agent, or Firm* — Simpson & Simpson, PLLC

(57) ABSTRACT

A method is provided for detecting a cancer in an individual, the method comprising detection of a deletion in the nucleic acid sequence between residues 10743 and 14125 in mitochondrial DNA by extracting the mitochondrial DNA (mtDNA) from the biological sample obtained from the individual and quantifying the amount of mtDNA in the sample having a deletion in the nucleic acid sequence between approximately residues 10743 and 14125 of the mtDNA genome, and comparing the amount of mtDNA in the sample having the deletion to at least one known reference sample. Kits for conducting the method are also provided.

28 Claims, 7 Drawing Sheets

Specification includes a Sequence Listing.

(56) References Cited

FOREIGN PATENT DOCUMENTS

| EP | 1 266 970 | 12/2002 |
|---|---|---|
| JP | 11-113597 | 4/1999 |
| WO | WO 98/23632 | 6/1998 |
| WO | WO 00/63441 | 10/2000 |
| WO | WO 01/68923 | 9/2001 |
| WO | WO 02/22873 | 3/2002 |
| WO | WO 02/101086 | 12/2002 |
| WO | WO 03/078661 | 9/2003 |
| WO | WO 06/11029 | 10/2010 |

OTHER PUBLICATIONS

Armstrong, B.K. (2004). How sun exposure causes skin cancer: an epidemiological perspective. In Prevention of Skin Cancer, Hill, D., Elwood, J.M. & English, D.J. (eds), vol. 3. pp. 89-116. Cancer Prevention—Cancer Causes. Kluwer Acedemic Publishers.
Armstrong, B.K. & Kricker, A. (2001). The epidemiology of UV induced skin cancer. J Photochem Photobiol B, 63, 8-18.
Berneburg, M., Gattermann, N., Stege, H., Grewe, M., Vogelsang, K., Ruzicka, T. & Krutmann, J. (1997). Chronically ultraviolet-exposed human skin shows a higher mutation frequency of mitochondrial DNA as compared to unexposed skin and the hematopoietic system. Photochem Photobiol, 66, 271-5.
Berneburg, M., Plettenberg, H., Medve-Konig, K., Pfahlberg, A., Gers-Barlag, H., Gefeller, O. & Krutmann, J. (2004). Induction of the photoaging-associated mitochondrial common deletion in vivo in normal human skin. J Invest Dermatol, 122, 1277-83.
Boukamp, P., Petrussevska, R.T., Breitkreutz, D., Hornung, J., Markham, A. & Fusenig, N.E. (1988). Normal keratinization in a spontaneously immortalized aneuploid human keratinocyte cell line. J Cell Biol, 106, 761-71.
Croteau, D.L. & Bohr, V.A. (1997). Repair of oxidative damage to nuclear and mitochondrial DNA in mammalian cells. JBiol Chem, 272, 25409-12.
Degoul, F., Nelson, I., Amselem, S., Romero, N., Obermaier-Kusser, B., Ponsot, G., Marsac, C. & Lestienne, P. (1991). Different mechanisms inferred from sequences of human mitochondrial DNA deletions in ocular myopathies. Nucleic Acids Res, 19, 493-6.
Durham, S.E., Krishnan, K.J., Betts, J. & Birch-Machin, M.A. (2003). Mitochondrial DNA damage in non-melanoma skin cancer. Br J Cancer, 88, 90-5.
Koch, H., Wittern, K.P. & Bergemann, J. (2001). In human keratinocytes the Common Deletion reflects donor variabilities rather than chronologic aging and can be induced by ultraviolet A irradiation. J Invest Dermatol, 117, 892-7.
Ledoux, S.P., Patton, N.J., Avery, L.J. & Wilson, G.L. (1993). Repair of N-methylpurines in the mitochondrial DNA of xeroderma pigmentosum complementation group D cells. Carcinogenesis, 14, 913-7.
Mita, S., Rizzuto, R., Moraes, C.T., Shanske, S., Arnaudo, E., Fabrizi, G.M., Koga, Y., Dimauro, S. & Schon, E.A. (1990). Recombination via flanking direct repeats is a major cause of large-scale deletions of human mitochondrial DNA. Nucleic Acids Res, 18, 561-7.
Moraes, C.T., Ricci, E., Petruzzella, V., Shanske, S., Dimauro, S., Schon, E.A. & Bonilla, E. (1992). Molecular analysis of the muscle pathology associated with mitochondrial DNA deletions. Nat Genet, 1, 359-67.
Moraes, C.T., Sciacco, M., Ricci, E., Tengan, C.H., Hao, H., Bonilla, E., Schon, E.A. & Dimauro, S. (1995). Phenotype-genotype correlations in skeletal muscle of patients with mtDNA deletions. Muscle & Nerve, 3, S 150-3.
Schon, E.A., Rizzuto, R., Moraes, C.T., Nakase, H., Zeviani, M. & Dimauro, S. (1989). A direct repeat is a hotspot for large-scale deletion of human mitochondrial DNA. Science, 244, 346-9.
Sciacco, M., Bonilla, E., Schon, E.A., Dimauro, S. & Moraes, C.T. (1994). Distribution of wild-type and common deletion forms of mtDNA in normal and respiration-deficient muscle fibers from patients with mitochondrial myopathy. Hum Mol Genet, 3, 13-9.
Shoffner, J.M., Lott, M.T., Voljavec, A.S., Soueidan, S.A., Costigan, D.A. & Wallace, D.C. (1989). Spontaneous Kearns-Sayre/chronic external ophthalmoplegia plus syndrome associated with a mitochondrial DNA deletion: a slip-replication model and metabolic therapy. Proc Natl Acad Sci USA, 86, 7952-6.
Alonso, A. C Alves, M.P. Suarez-Mier, C Albarran, L Pereira, L Fernandez De Simon, P. Martin, O Garcia, L Gusmao, M Sancho, A Amorim 2005. J Clin Pathology 58: 83-86.
Anderson S, et al., Sequence and Organization of the human mitrochondrial genomre. Nature 290:457-464, 1981.
Andrews RM, et al., Reanalysis and revision of the Cambridge references sequence for human mitochondrial DNA. Nature Genetics 23(2):147, 1999.
Berneburg M, et al., Singlet oxygen mediates the UVA-induced generation of the photoaging-associated mitochondrial common deletion. J. Biol. Chem. 274(22):15345-15349, 1999.
Berthon P, Valeri A, Cohen-Akeninc A, Drelon E, Paiss T, Wohr G, Latil A et al., Predisposing gene for early-onset prostate cancer, localized on chromosome. 1q42.2-43. Am. J. Hum. Genet., 62: 1416-1424, 1998.
Birch-Machin MA, et al.,Study of skeletal muscle mitochondrial dysfunction. Methods in Toxicology, vol. 2, 51-69,1993.
Birch-Machin MA, et al., Mitochondrial DNA deletions in human skin reflect photo rather that chronologic aging. J. Invest.Dermatol 110:149-152 1998.
Birch-Machin MA, Taylor RW, Cochran B, Ackrell BAC, Turnbull DM. Late-onset optic atrophy ataxia, and myopathy associated with a mutation of a complex II gene. Ann Neurol 48: 330-335, 2000(b).
Birch-Machin MA, Mitochondria and skin disease. Clin. Exp. Dermatol,. 25(2), 141-146, 2000 (c).
Birch-Machin MA and Krishnan K. Abstracts—Mitochondria 2001 Meeting San Diego, CA, Feb. 28-Mar. 2, 2001, 1, p. 45 (2001), p. 46.
Birch-Machin MA, Lindsey J. Lusher M and Krishnan K. Mitochondrion1, 1 (Suppl) 1, S30 (2001).
Bogliolo, M, et al., Detection of the 4977 bp mitorchondrial DNA deletion in human atherosaclerotic lesions Mutagenesis, 14: 77-82, 1999.
Brierley EJ, Johnson MA, Lightowlers RN, James O, Turnbull DM., Role of mitochondrial DNA mutations in human aging: Implications for the central nervous system and muscle. Ann Neurol 43(2):217-223, 1998.
Brockington, et al., A tandem duplication in the D-loop of human mitochondrial DNA is associated with deletions in mitochondrial myopathies. Nature Genet 4:67-71, 1993.
Brown, M.D., et al., Clustering of Caucasian Leber hereditary optic neuropathy patients containing the 11778 or 14484 mutations on mtDNA lineage. Am J. Hum Genet, 60: 381-387, 1997.
Buttyan R, Sawczuk IS, Benson MC, Siegal JD, Olsson CA., Enhanced expression of the c-myc protooncogene in high grade human prostate cancer. Prostate 11:327-337, 1987.
Cairns P, Okami K, Halachmi S, Halachmi N, Esteller M, Herman JG, Jen J et al., Frequent inactivation of PTEN/MMAC1 in primary prostate cancer. Cancer Res 57:4997-5000, 1997.
Chinnery PF, Howel N, Turnbull DM. Clinical mitochondrial genetics. J. Med. Genet.; J.Med.Genet.; 36: 425-436, 1999.
Chinnery PF and Turnbull DM., Mitochondrial DNA and disease. Lancet 354 (supplement 1): 17-21, 1999.
Cormier-Daire et al., Mitochondrial DNA rearrangements with onset as chronic diarrhea with villous atrophy, The Journal of Pediatrics, Jan. 1994, vol. 124, No. 1, pp. 63-70.
Chomyn A, et al., Melas mutation in mtDNA binding-site fortranscription termination factor causes defects in protein-synthesis and in respiration but no change in levels upstream and downstream mature transcripts. Proc. Natl. Acad. Sci. USA 89(10):4221-4225, 1992.
Corral-Debrinski et al., Association of Mitochondrial-DNA Damage with aging and coronary atheroscolerotic heart-disease. Mutat Res, 275: 169-180, 1992.

(56) References Cited

OTHER PUBLICATIONS

Cortopassi G. A. and Arnheim, N. Detection of a specific mitochondiral DNA deletion in tissues of older humans, Nucleic Acids Research. 18, 6927-6933 1990.
Cortopassi G, Wang E., Modelling the effects of age-related mtDNA mutation accumulation-complex-I deficiency, superoxide and cell-death. Biochim Biophys Acta 1271(1):171-176,1995.
Croteau DL, Stierum RH, Bohr VA, Mitrochondrial DNA repair pathways. Mutat Res 434(3):137-148, 1999.
Easton RD, Merriwether AD, Crews DE, and Ferrell RE., mtDNA varation in the Yanomami Evidence for additional New World founding lineages. Am. J. Hum. Genet. 59:213-225, 1996.
Fahn H, Wang L, Hseith R, Chang S, Kao S, Huang M, and Wei Y. Age-related 4977 bp Deletion in Human Lung Mitochondrial DNA. American Journal of Respiratory Critical Care Medicine, 154:1141-1145, 1996.
Finegold D., Diagnosis: The Promise of DNA Analysis in Understanding Mitrochondrial Disease; Mitochondrial and Metabolic Disorders, p. 12, 1997.
Flanagan N, et al., Pleiotropic effects of the melanocortin 1 receptor (MC1R) gene on human pigmentation. Hum Mol Genet 9 (17):2531-2537, 2000.
Petros, John A. et al., mtDNA mutations increase tumorigenicity in prostate cancer, PNAS, Jan. 18, 2005, vol. 102, No. 3, pp. 719-724.
Flanagan N, Ray AJ, Todd C, Birch-Machin MA and Rees JL. The relation between melanocortin 1 receptor genotype and experimentally assessed ultraviolet radiation sensitivy. J Invest. Dermatol (2001) 117(5) 1314-1317.
Gattermann, N, Berneburg, M, Heinisch, J, Aul, C, Schneider, W., Detection of the ageing-associated 5-kb common deletion of mitochondrial-DNA in blood and bone marrow of hematologycally normal adults-absence of the deletion in clonal bone marrow disorders. Leukemia 9(10): 1704-10, 1995.
Habano W, Nakamura S, Sugai T., Microsatellite instability in the mitochondrial DNA of colorectal carcinomas: Evidence for mismatch repair systems in mitrochondrial genome, Oncogene 17 (15):1931-1937, 1998.
Harding RM, et al., Evidence for variable selective pressures at MC1R. Am. J. Hum. Genet. 66, 1351-1361, 2000.
Hattori et al, Age-dependant increase in deleted mitochondrial DNA in the human heart: possible contributory factor to presbycardia, AM. Heart J., 121, 1735-1742, 1991.
Hayashi J, Ohta S, Kikuchi A, Takemitsu M, Goto Y, Nonaka I., Introduction of disease-related mitochondrial-DNA deletions into hela-cells lacking mitochondrial-DNA results in mitochondrial dysfunction. Proc Natl Aced Sci USA 88 (23): 10614-10618, 1991.
Hayward SW, Grossfeld GD, Tlsty TD, Cunha GR., Genetic and epigenetic influences in prostatic carcinogenesis—(Review). Int J Oncol 13:35-47, 1998.
Healy E, Birch-Machin MA, Rees JL. Chapter 11. The Human Melanocortin 1 Receptor Gene. In the Melanocortin Receptors (Cone RD (ed)). Humana Press Inc. New Jersey, USA, 1999.
Healy E, et al. Melanocortin-1-receptor gene and sun sensitivity in individuals without red hair. Lancet 355. 9209, 1072-1073, 2000.
Hsieh, RH, et al., Age-Dependent Respiratory Function Decline and DNA Deletions in Human Muscle Mitochondria, Biochemistry and Molecular Biology Int'l, vol. 32, No. 6, Apr. 1994, pp. 1009-1022.
Ikebe et al., Increase of deleted mitochondrial DNA in the striatum in Parkinson's disease and senescence, Biochem. Biophys. Res. Commun. 170, 1044-1048, 1990.
Katayama et al., Deleted mitochondrial DNA in the skeletal muscle of aged individuals, Biochem. Int., 25, 47-56 1991.
Kleinle S, et al., Detection and characterization of mitochondrial DNA rearrangements in Pearson and Kearns-Sayre syndromes by PCR. Human Genet. 100:643-650, 1997.
Konishi N, Cho M, Yamamoto K, Hiasa Y. Genetic changes in prostate cancer. Pathol. Int. 47:735-747, 1997.
Krishnan K and Birch-Machin MA. British Society for Investigative Dermatology Annual Meeting. British Journal of Dermatology (2002), 146, (p. 723).

Ledoux SP, et al. Repair of alkylation and oxidative damage in mitochondrial DNA. Mutat Res 434(3):149-159, 1999.
Lee HC, et al. Ageing-associated tandem duplications in the D-loop of mitochondrial DNA of human muscle. FEBS Letters 354:79-83, 1994.
Lee HC, Lu CY, Fahn HJ, Wei YHu. Aging-and smoking-associated alteration in the relative content of mitochondrial DNA in human lung. Federation of European Biochemical Societies, 441:292-296, 1998.
Lee HC, et al. Concurrent increase of oxidative DNA damage and lipid peroxidation together with mitochondrial DNA mutation in human lung tissues during aging—Smoking enhances oxidative stress on the aged tissues. Arch. Biochem. Biophys. 362(2): 309-16, 1999.
Liu CS, Kao SH, Wei YH. Smoking-Associated Mitochondrial DNA Mutations in Human Hair Follicles. Environ. Mol. Mutagen 30(1): 47-55, 1997.
Lopez, J.V. et al. (1994) Numt, a recent transfer and tandem amplification of mitochondrial DNA to the nuclear genome of the cat. J. Mol. Evol. 39, 174-190.
Lowes S, Krishnan K, Lindsey J, Lusher M and Brich-Machin MA. British Society for Investigative Dermatology Annual Meeting. British Journal of Dermatology (2002), 146, 736.
Meibner C, Von Wurmb N, Oehmichen M., Detection of the age-dependent 4977 bp deletion of mitochondrial DNA; a pilot study, Int. J. Legal Med. 110: 288-291, 1997.
Michikawa Y, Mazzucchelli F, Bresolin N, Scarlato G, Attardi G., Aging-Dependent Large Accumulation of Point Mutations in the Human mtDNA Control Region for Replication. Science 286: 774-779, 1999.
Miquel J, De Juan E, Sevila I. Oxygen-induced mitochondrial damage and aging. EXS 62:47-57, 1992.
Nachman MW, Brown WM, Stoneking M, Aquardo CF., Nonneutral Mitochondrial DNA Variation in Humans and Chimpanzees. Genetics 142:953-963, 1996.
Naviaux, RK., Mitochondrial Disease—Primary Care Physican's Guide. Psy-Ed. Corp D/B/A Exceptional Parents Guide: 3-10, 1997.
Yu, B, et al.; DNA mutation detection using denaturing high-performance liquid chemoatography (DHPLC). Current protocols in human genetics 19, 7.10.1-14, 1998.
Ozen M, et al., Telomeric DNA Marker for Human Prostate Cancer Development?. Prostate 36:264-271, 1998.
Pang et al., Human Skin Mitochondrial DNA Deletions Associated with Light Exposure. Arch. Biochem. Biophys. 312:(2), 534-538, 1994.
Parsons TJ, et al., A high observed substitution rate in the human mitochondrial DNA control region. Nature Genet. 15 (4):363-368, 1997.
Pascucci B, et al., DNA repair of UV photoproducts and mutagenesis in human mitochondrial DNA. J.Mol.Biol. 273 (2):417-427, 1997.
Penta JS, Johnson FM, Wachsman JT, Copeland, W.C., Mitochondrial DNA in human malignancy, Mut. Res. 488, 119-133, 2001.
Polyak K, et al., Somatic mutations of the mitochondrial genome in human colorectal tumours. Nature Genet. 20 (3):291-293, 1998.
Harman, K.E. et al., Defining Target Antigens in Linear IgA Disease Using Skin From Patients with Inherited Genodermatoses as Substrates for Indirect Immunoflurescence Microscopy; Br. J. of Derm. 138, p. 733 (1998).
Ray AJ, et al. Abstract of the British Society for Investigative Dermatology, Annual Meeting—Cardiff, Apr. 7-9, 1999, Brit.J. Dermatol.140:788, 1999.
Ray AJ, Turner R, Nikaido O, Rees JL, Birch-Machin MA., The spectrum of mitochondrial DNA deletions is a ubiquitous marker of ultraviolet radiation exposure in human skin. J. Invest. Dermatol 115(4):674-679, 2000.
Rees JL. Skin cancer [Gorlin's Syndrome], In:The Genetic Basis of Human Cancer, eds Vogelstein B, Kinzler K. New York: McGraw-Hill, pp. 527-536, 1998.
Rehman I, Quinn AJ, Healy E, Rees JL. High-frequency of loss of heterozygosity in actinic keratoses, a usually benign disease. Lancet 344: 788-789, 1994.
Rehman I, Takata M, Wu YY, Rees JL. Genetic change in actinic keratoses. Oncogene 12: 2483-2490, 1996.

(56) References Cited

OTHER PUBLICATIONS

SAS Enterprise Mining Users Guide, SAS Inc., 2000.
Sawyer E, Van Houten B., Repair of DNA damage in mitochondria. Mutation Res: 434(3):161-176, 1999.
Schurr TG, Ballinger SW, Gan Y, Hodge JA, Merriwether DA, Lawrence DN, Knowler WC, Weiss KM, and Wallace DC., Amerindian Mitochondial DNAs Have Rare Asian Mutations at high Frequencies, Suggesting They Derived from Four Primary Maternal Lineages. Am. J. Hum. Genet. 46:613-623, 1990.
Seidman, M.D. et al., Mitochondrial DNA deletions associated with aging and presbyacusis. Arch. Otolaryngol Head Neck Surg., 123: 1039-1045, 1997.
Shankey TV, Jin JK, Dougherty S, Flanigan RC, Graham S, Pyle JM., DNA-ploidy and proliferation heterogeneity in human prostate cancers. Cytometry 21:30-39, 1995.
Shay JW, Werbin H., Are Mitrochondrial DNA Mutations Involved in the Carcinogenic Process?. Mutat. Res:186: p. 149-160, 1987.
Sherrat EJ, Thomas AW, Alcolado. Mitochondrial DNA defects: A widening clinical spectrum of disorders. JC., Clin. Sci. 92:225-235, 1997.
Shoffner JM, Brown MD, Torroni A, Lott MT, Cabell MF, Mirra SS, Beal MF, Yang C, Gearing M, Salvo R, Watts RL, Juncos JL, Hansen LA, Crain BJ, Fayad M, Reckford CL, and Wallace DC., Mitochondrial DNA Variants Observed in Alzheimer Disease and Parkinson Disease Patients, Genomics 17: 171-184, 1993.
Smith DG, Malhi RS, Eshleman J, Lorenz JG and Kaestle FA., Distribution of mtDNA haplogroup X among Native North Americans. Am. J. Hum. Genet. 110:271-284, 1999.
Smith R, Birch-Machin MA, Rees JL. Melanocortin 1 receptor variants in an Irish population. J. Invest. Dermatol. 111: (1) Jul. 1998, 101-104.
Tamura S, et al. Mutations in mitochondrial control region DNA in gastric tumours of Japanese patients. Eur.J.Cancer [A] 35 (2):316-319, 1999.
Tanaka, M. et al, 1996, Automated sequencing of mtDNA, Methods Enzymol. 264: 407-421.
Taniike, M. et al., Mitochondrial transfer rnaile mutation in fatal cardiomyopathy. BioChem BioPhys Res Comun, 186: 47-53, 1992.
Taylor RW, Birch-Machin MA, Bartlett K, Turnbull DM., The control of mitoch. oxidations by complex-III in rat muscle and liver-mitochondria-implications for our understanding of mitochondrial cytopathies in man. J Biol Chem, 269, 3523-3528 1994.
Torii K. et al., Aging-associated deletions of human diaphragmatic mitochondrial DNA, Am. J. Respir. Cel.l Mol. Biol. in press 1992, p. 543-549.
Valnot, Isabelle, et al., A mitochondrial cytochrome b mutation but no mutations of nuclearly encoded subunits in ubiquinol cytochrome c reductase (complex III) deficiency, Human Genetics (1999) 104: 460-466.
Van Den Bosch BJC, et al., Mutation analysis of the entire mitochondrial genome using denaturing high performance liquid chromatography. Nucleic Acids Res. 28: 89, 2000.
Von Wurmb, N, Oehmichen, M, Meissner, C., Demonstration of the 4977 bp deletion in human mitochondrial DNA from intravital and postmortem blood. Mutat Res. 422:247-254, 1998.
Wallace DC., Diseases of the mitochondrial-DNA. Annu Rev Biochem, 61: 1176-1212, 1992.
Wallace DC. Mitochondrial-DNA sequence variation in human-evolution and disease. Proc. Natl. Acad. Sci. USA 91: 8739-8746, 1994.
Wald and Wallace, D.C., Mitochondrial Diseases in man and Mouse. Science, 5(283): 1482-1497, 1999.
Wallace et al., Mitochondiral DNA Mutation Associated with Leber's Hereditary Optic Neuropathy, Science, 1427-1429; 1988.
Walsh PC, Partin, AW, Family history facilitates the early diagnosis of prostate carcinoma. Cancer 80:Nov. 1, 1997, vol. 80, No. 9; pp. 1871-1874.
Ward RH, Frazier BL, Dew-Jager K, Paabo S., Extensive mitochondrial diversity within a single amerindian tribe. Proc. Natl. Acad. Sci. USA 88:8720-8724, 1991.
Wei YH, Pang C, You B, Lee H., Tandem Duplications and Large-Scale Deletions of Mitochondrial DNA Are Early Molecular Events of Human Aging Process, Annals NY Acad. of Sciences 786:82-101, 1996.
Wei YH. Mitochondrial DNA Mutations and Oxidative Damage in Aging and Diseases: An Emerging Paradigm of Gerontology and Medicine; Proc. of the Nat. Sci. Council of the ROC, vol. 22(2):1998, pp. 55-67 1997.
Weinstock MA: Epidemiology of ultraviolet radiation. In: JJ Stern RS, MacKie RM and Weinstock MA, Grob (eds) Epidemiology, Blackwell (UK). pp. 121-128, 1998.
Wu & Wallace., The ligation amplification reaction (LAR)—amplification of specific DNA-sequences using sequential rounds of template-dependent ligation. Genomics, 4:560, 1989.
Xu J, et al., Evidence for a prostate cancer susceptibility locus on the X chromosome. Nature Genet 20: 175-179,1998.
Yamaguchi KT, et al., Measurement of free-radicals from smoke-inhalation and oxygen exposure by spin trapping and esr spectroscopy. Free Radical Res. Commun. 16(3):167-74, 1992.
Yeh, J.J., et al., Somatic mitochondrial DNA (mtDNA) mutations in papillary thyroid carcinomas and differential mtDNA sequence variants in cases with thyroid tumours. Oncogene Journal, 19: 2060-2066, 2000.
Yen et al., Ageing-associated 5kb deletion in human liver mitochondrial DNA, Biochem., Biophys., Res. Commun., 178, 124-131 1991.
Yen et al., Age-dependent 6 kb deletion in human liver mitochondrial DNA, Biochem. Int. 26, 457-468 1992.
Zeviani M, et al. Nucleus-driven Multiple Large-Scale Deletions of the Human Mitochondrial Genome: A New Autosomal Dominant Disease. Am. J. Hum. Genet. 47:904-914, 1990.
Zhang et al., Multiple mitochondiral DNA deletions in an elderly human individual, FEBS Lett, 297, 34-38 1992.
Zhang, C., et al., Occurrence of a Particular Base Substitution (3243 A to G) in Mitochondrial DNA of Tissues of Ageing Humans. BioChem. BioPhys. Res. Comun., 195: 1104-1110, 1993.
Jessie B et al., "Accumulation of mitochondrial DNA deletions in the aging prostate." Proceedings of the American Association for Cancer Research Annual, vol. 42, Mar. 2001, pp. 862-863, XP001153110. 92nd Annual Meeting of the American Association for Cancer Research; New Orleans, LA, USA; Mar. 24-28, 2001. ISSN: 0197-016X.
Thayer R et al., "Mitochondrial DNA mutations and/or deletions in prostate cancers," Proceedings of the American Association for Cancer Research Annual, vol. 42, Mar. 2001, pp. 532-533, XP001153105. 92nd Annual Meeting of the American Association for Cancer Research, New Orleans, LA, USA; Mar. 24-28, 2001. ISSN: 0197-016X.
Petros JA et al., "Mitochondrial DNA point mutations are common in prostate cancer and enhance malignant phenotype," Proceedings of the American Association for Cancer Research Annual, vol. 42, Mar. 2001, p. 517, XP001153111. 92nd Annual Meeting of the American Association for Cancer Research, New Orleans, LA, USA; Mar. 24-28, 2001. ISSN: 0197-016X.
Jeronimo C. et al., "Mitochondrial mutations in early stage prostate cancer and bodily fluids," Proceedings of the American Association for Cancer Research Annual, vol. 42, Mar. 2001, p. 63, XP001153112. 92nd Annual Meeting of the American Association for Cancer Research, New Orleans, LA, USA; Mar. 24-28, 2001. ISSN: 0197-016X.
Eshaghian A. et al., "Alterations of mitochondrial DNA in aging skin and in non-melanoma skin cancers," Proceedings of the American Association for Cancer Research Annual, vol. 43, Mar. 2002, pp. 304-305, XP001153120, 93rd Annual Meeting of the American Association for Cancer Research, San Francisco, California, USA, Apr. 6-10, 2002, ISSN: 0197-016X.
Hardy et al. Ethnic Differences and Disease Phenotypes. Science 2003 vol. 300, p. 737-781.
Hirschorn et al. A comprehensive review of genetic association studies. 2002 Genetics in Medicine p. 45-61.
Lucentini, J., Gene association studies typically wrong, reproducible gene-disease associations are few and far between, The Scientist, Dec. 20, 2004, p. 20.

(56) References Cited

OTHER PUBLICATIONS

Ioannidis J et al., Replication validity of genetic association studies. Nature Genetics 2001 vol. 29 p. 306-309.
Buzzi et al. mtDNA A3243G MELAS mutation is not associated with multigenerational female migraine. Neurology 2000 vol. 54 p. 1005-1007 Abstract.
Kogelnik Andreas M et al., "MITOMAP: A human mitochondrial genome database—1998 update," Nucleic Acids Research, Oxford University Press, Surry, GB, vol. 26, No. 1, 1998, pp. 112-115, XP002966479, ISSN: 0305-1048.
Bandelt Hans-Jurgen et al., "What is 'novel' mtDNA mutation- and does 'novelty' really matter?" Journal of Human Genetics 2006, vol. 51, No. 12, 2006, pp. 1073-1082, XP002450142, ISSN: 1434-5161.
Croation Medical Journal, vol. 42, No. 3, 2001, Thomas J. Parsons et al., "Increasing the forensic discrimination of mitochondrial DNA testing through analysis of the entire mitochondrial DNA genomes", pp. 304-309.
Nature, vol. 408, Dec. 2000, Max Ingman et al., "Mitochondrial genome variation and the origin of modern humans," pp. 708-713.
Genomics, vol. 55, 1999, Barbara C. Levin et al., "A human mitochondrial DNA standard reference material for quality control in forensic identification, medical diagnosis, and mutation detection," pp. 135-146.
Biotechniques, vol. 32, No. 1, Jan. 2002, H. Andreasson et al.: "Mitochondrial Sequence Analysis for Forensic Identification Using Pyrosequencing Technology," pp. 124-133.
Harbottle et al., Implications of Using the ND1 Gene as a Control Region for Real-Time PCR Analysis of Mitochondrial DNA Deletions in Human Skin. The Journal of Investigative Dermatology: 1518-1521, 2004.
Maitra, A. et al. The Human MitoChip: A High-Throughput Sequencing Microarray for Mitochondrial Mutation Detection. Genome Res. May 2004, vol. 14, No. 5, pp. 812-819 (plus cover page), ISSN 1088-9051.
Krishnan, K.J. et al. The Use of a 3895 bp Mitochondrial DNA Deletion as a Marker for Sunlight Exposure in Human Skin. J. Invest. Dermatol. Dec. 2004, vol. 123, No. 6, pp. 1020-1024. ISSN 0022-202X.
Prithivirajsingh, S. et al. Accumulation of Common Mitochondrial DNA Deletion Induced by Ionizing Radiation. FEBS Lett. Aug. 2004, vol. 571, pp. 227-232. ISSN 0014-5793.
Chabi, B. et al., Quantification of Mitochondrial DNA Deletion, Depletion,and Overreplication: Application to Diagnosis. Clin. Chem. Aug. 2003, vol. 49, No. 8, pp. 1309-1317. ISSN 0009-9147.
Mutation Research, 2000, vol. 468, pp. 35-43. CC to TT mutation in the mitochondrial DNA of normal skin: relationship to ultraviolet exposure.
Nucleic Acids Res., Denaturing high performance liquid chromatography (DHPLC) used in the detection of germline and somatic mutations. vol. 26, No. 6, pp. 1396-1400, 1998.
Parrella P. et al., Detection of Mitochondrial DNA Mutations in Primary Breast Cancer and Fine-Needle Aspirates, Cancer Research, 61, 7623-7626, 2001.
Chen, J. et al., Extensive Somatic Mitochondrial Mutations in Primary Prostate Cancer Using Laser Capture Microdissection, Cancer Research, 62, 6470-6474, 2002.
Fliss, M. et al., Facile Detection of Mitochondrial DNA Mutations in Tumors and Bodily Fluids, Science, 287, 2017-2019, 2000.
Jeronimo, C. et al., Mitochondrial mutations in early stage prostrate cancer and bodily fluids, Oncogene, 20, 5195-5198, 2001.
Chen, J. et al., Simultaneous generation of multiple mitochondrial DNA mutations in human prostrate tumors suggests mitochondrial hyper-mutagenesis, Carcinogenesis, vol. 24, No. 9, pp. 1481-1487, 2003.
Bugart, L. et al., Somatic Mitochondrial Mutation in Gastric Cancer, American Journal of Pathology, 147, 1105-1111, 1995.
Jessie, B. et al., Accumulation of mitochondrial DNA deletions in the malignant prostate of patients of different ages, Experimental Gerontology 37, 169-174, 2001.
Zhu, Weizhu, M.D. et al., Large-scale mitochondrial DNA deletion mutations and nuclear genome instability in human breast cancer. Cancer Detection and Prevention, 28, pp. 119-126 copyrighted 2004 International Society for Preventative Oncology.
He, L. et al.;"Detection and quantification of mitochondrial DNA deletions in individual cells by real-time PCR." Nucleic Acids Research [online], Jul. 15, 2002 (Jul. 15, 2002) {retrieved on Apr. 3, 2008], vol. 30, No. 14, p. e68, ISSN:1362-4962. Retrieved from Internet: <URL: http://nar.oxfordjournals.org/cgi/reprint/30/14e68>.
Maki, J. et al.; "Mitochondrial genome deletion aids in the identification of false-and true-negative prostate needle core biopsy specimens," American Journal of Clinical Pathology, Jan. 2008, vol. 129, No. 1, pp. 57-66, ISSN: 0002-9173.
Huoponen, Kirsi, Leber hereditary optic neuropathy: clinical and molecular genetic findings, Neurogentics (2001) 3: 119-125.
Huang GM, Ng WL, Farkas J, He L, Liang HA, Gordon D, Hood R., Genomics 59(2): 178-86, 1999.
Landis SH, Murray T, Volden S, Wingo PA. Cancer J. Clin 49:8-31. Mitomap: A human mt genome database (www.gen.emory.edu/mitomap.html).
Wei YH., Proceedings of the Nat Sci. Council of the Republic of China. Apr. 22(2):5567, 1998.
Woowell DA., National Ambulatory Medical Care Survey: 1997 Summary. Advance data from vital and health statistics; No. 305. Hyattsville, Maryland: National Center for Health Statistics. 1999.
Harbottle and Ma Birch-Machin A. "Real-time PCR analysis of a 3895 bp mitochondrial DNA deletion in nonmelanoma skin cancer and its use as a quantitative marker for sunlight exposure in human skin," British Journal of Cancer, Nature Publishing Group, London, GB, vol. 94, No. 12, Jan. 1, 2006 (Jan. 1, 2006), pp. 1887-1893.
Linnane, Anthony W. et al., Mitochondrial Gene Mutation: The Ageing Process and Degenerative Diseases, 22 Biochemistry International, pp. 1067-1076 (1990).
Modica-Napolitano, Josephine S. et al., Mitochondria as Targets for Detection and Treatment of Cancer, 4 Expert Reviews in Molecular Medicine. pp. 1-19 (2002).
Taanman, J.W. et al., Molecular Mechanisms in Mitochondrial DNA Depletion Syndrome, 6 Human Molecular Genetics. pp. 935-942 (1997).
Ward, R.H.et al., Genetic and Linguistic Differentiation in the Americas, 90 Proceedings of the National Academy of Sciences, pp. 10663-10667 (1993).
Kajander, Olli A., Anja T. Rovio, Kari Majamaa, Joanna Poulton, Johannes N. Spelbrink, Ian J. Holt, Pekka J. Karhunen and Howard T. Jacobs, Human mtDNA sublimons resemble rearranged mitochondrial genoms found in pathological states, Sep. 25, 2000, pp. 2821-2835, vol. 9, No. 19, Human Molecular Genetics, Oxford University Press.
Chuanzhong YE et al., Quantitative analysis of mitochondrial DNA 4977-bp deletion in sporadic breast cancer and benign breast diseases. Breast Cancer Research and Treatment, vol. 108, No. 3, May 31, 2007 (May 31, 2007), pp. 427-434, XP002591332. ISSN: 0167-6806.
Tan, Duan-Jun et al., Comprehensive scanning of somatic mitochondrial DNA mutations in breast cancer. Cancer Research, vol. 62, No. 4, Feb. 15, 2002 (Feb. 15, 2002), pp. 972-976, XP002591333. ISSN: 0008-5472.

\* cited by examiner ns2-example

SEQUENCE LISTING

```
<160> NUMBER OF SEQ ID NOS: 10

<210> SEQ ID NO 1
<211> LENGTH: 3379
<212> TYPE: DNA
<213> ORGANISM: Homo sapiens

<400> SEQUENCE: 1
cctaaaccta ctccaatgct aaaactaatc gtcccaacaa ttatattact accactgaca      60
tgactttcca aaaacacat aatttgaatc aacacaacca cccacagcct aattattagc     120 atcatcctc tactattttt taaccaaatc aacaacaacc tatttagctg ttccccaacc     180
```

```
ttttcctccg accccctaac aaccccccctc ctaatactaa ctacctgact cctacccctc      240
acaatcatgg caagccaacg ccacttatcc agtgaaccac tatcacgaaa aaaactctac      300
ctctctatac taatctccct acaaatctcc ttaattataa cattcacagc cacagaacta      360
atcatatttt atatcttctt cgaaaccaca cttatcccca ccttggctat catcacccga      420
tgaggcaacc agccagaacg cctgaacgca ggcacatact tcctattcta caccctagta      480
ggctcccttc ccctactcat cgcactaatt tacactcaca caccctaggc tcactaaac       540 attctactac tcactctcac tgcccaagaa ctatcaaact cctgagccaa caacttaata      600
tgactagctt acacaatagc ttttatagta aagatacctc tttacggact ccacttatga      660
ctccctaaag cccatgtcga agcccccatc gctgggtcaa tagtacttgc cgcagtactc      720
ttaaaactag gcggctatgg tataatacgc ctcacactca ttctcaaccc cctgacaaaa      780
cacatagcct acccccttcct tgtactatcc ctatgaggca taattataac aagctccatc      840
tgcctacgac aaacagacct aaaatcgctc attgcatact cttcaatcag ccacatagcc      900
ctcgtagtaa cagccattct catccaaacc ccctgaagct tcaccggcgc agtcattctc      960
ataatcgccc acgggcttac atcctcatta ctattctgcc tagcaaactc aaactacgaa     1020
cgcactcaca gtcgcatcat aatcctctct caaggacttc aaactctact cccactaata     1080 gcttttttgat gacttctagc aagcctcgct aacctcgcct tacccccac tattaaccta      1140 ctgggagaac tctctgtgct agtaaccacg ttctcctgat caaatatcac tctcctactt     1200
acaggactca acatactagt cacagcccta tactccctct acatatttac cacaacacaa     1260
tggggctcac tcacccacca cattaacaac ataaaaccct cattcacacg agaaaacacc     1320
ctcatgttca tacacctatc ccccattctc ctcctatccc tcaacccga catcattacc      1380 gggttttcct cttgtaaata tagtttaacc aaaacatcag attgtgaatc tgacaacaga     1440
ggcttacgac cccttattta ccgagaaagc tcacaagaac tgctaactca tgcccccatg     1500
tctaacaaca tggctttctc aacttttaaa ggataacagc tatccattgg tcttaggccc     1560
caaaattttt ggtgcaactc caaataaaag taataaccat gcacactact ataaccaccc     1620
taaccctgac ttccctaatt cccccatcc ttaccacccc cgttaaccct aacaaaaaaa     1680
actcataccc ccattatgta aaatccattg tcgcatccac ctttattatc agtctcttcc     1740
ccacaacaat attcatgtgc ctagaccaag aagttattat ctcgaactga cactgagcca     1800
caacccaaac aacccagctc tccctaagct tcaaactaga ctacttctcc ataatattca     1860
tccctgtagc attgttcgtt acatggtcca tcatagaatt ctcactgtga tatataaact     1920
cagacccaaa cattaatcag ttcttcaaat atctactcat cttcctaatt accatactaa     1980
tcttagttac cgctaacaac ctattccaac tgttcatcgg ctgagagggc gtaggaatta     2040
tatccttctt gctcatcagt tgatgatacg cccgagcaga tgccaacaca gcagccattc     2100
aagcaatcct atacaaccgt atcggcgata tcggtttcat cctcgcctta gcatgattta     2160
tcctacactc caactcatga gacccacaac aaatagccct tctaaacgct aatccaagcc     2220
tcaccccact actaggcctc ctcctagcag cagcaggcaa atcagcccaa ttaggtctcc     2280 accctgact cccctcagcc atagaaggcc cacccagt ctcagcccta ctccactcaa       2340
gcactatagt tgtagcagga atcttcttac tcatccgctt ccacccccta gcagaaaata     2400
gcccactaat ccaaactcta acactatgct taggcgctat caccactctg ttcgcagcag     2460
tctgcgccct tacacaaaat gacatcaaaa aaatcgtagc cttctccact tcaagtcaac     2520
taggactcat aatagttaca atcggcatca accaaccaca cctagcattc ctgcacatct     2580
```

```
gtacccacgc cttcttcaaa gccatactat ttatgtgctc cgggtccatc atccacaacc      2640
ttaacaatga acaagatatt cgaaaaatag gaggactact caaaaccata cctctcactt      2700
caacctccct caccattggc agcctagcat tagcaggaat acctttcctc acaggtttct      2760
actccaaaga ccacatcatc gaaaccgcaa acatatcata cacaaacgcc tgagccctat      2820
ctattactct catcgctacc tccctgacaa gcgcctatag cactcgaata attcttctca      2880
ccctaacagg tcaacctcgc ttccccaccc ttactaacat taacgaaaat aaccccaccc      2940
tactaaaccc cattaaacgc ctggcagccg gaagcctatt cgcaggattt ctcattacta      3000
acaacatttc ccccgcatcc cccttccaaa caacaatccc cctctaccta aaactcacag      3060
ccctcgctgt cactttccta ggacttctaa cagccctaga cctcaactac ctaaccaaca      3120
aacttaaaat aaaatcccca ctatgcacat tttatttctc caacatactc ggattctacc      3180
ctagcatcac acaccgcaca atcccctatc taggccttct tacgagccaa aacctgcccc      3240
tactcctcct agacctaacc tgactagaaa agctattacc taaaacaatt tcacagcacc      3300
aaatctccac ctccatcatc acctcaaccc aaaaaggcat aattaaactt tacttcctct      3360
ctttcttctt cccactcat                                                   3379

<210> SEQ ID NO 2
<211> LENGTH: 30
<212> TYPE: DNA
<213> ORGANISM: Artificial Sequence
<220> FEATURE:
<223> OTHER INFORMATION: synthetic primer 3.4 kb deletion forward

<400> SEQUENCE: 2
tagactacgt acatactaac cctactccta                                        30

<210> SEQ ID NO 3
<211> LENGTH: 19
<212> TYPE: DNA
<213> ORGANISM: Artificial Sequence
<220> FEATURE:
<223> OTHER INFORMATION: synthetic primer 3.4 kb deletion reverse

<400> SEQUENCE: 3
gaggtaggat tggtgctgt                                                    19

<210> SEQ ID NO 4
<211> LENGTH: 21
<212> TYPE: DNA
<213> ORGANISM: Artificial Sequence
<220> FEATURE:
<223> OTHER INFORMATION: synthetic primer mtDNA genome forward

<400> SEQUENCE: 4
cgttccagtg agttcaccct c                                                 21

<210> SEQ ID NO 5
<211> LENGTH: 23
<212> TYPE: DNA
<213> ORGANISM: Artificial Sequence
<220> FEATURE:
<223> OTHER INFORMATION: synthetic primer mtDNA genome reverse

<400> SEQUENCE: 5
cactctttac gccggcttct att                                               23
```

```
<210> SEQ ID NO 6
<211> LENGTH: 20
<212> TYPE: DNA
<213> ORGANISM: Artificial Sequence
<220> FEATURE:
<223> OTHER INFORMATION: synthetic primer TNF nuclear gene forward

<400> SEQUENCE: 6
cctgccccaa tccctttatt                                                    20

<210> SEQ ID NO 7
<211> LENGTH: 21
<212> TYPE: DNA
<213> ORGANISM: Artificial Sequence
<220> FEATURE:
<223> OTHER INFORMATION: synthetic primer TNF nuclear gene reverse

<400> SEQUENCE: 7
ggtttcgaag tggtggtctt g                                                  21

<210> SEQ ID NO 8
<211> LENGTH: 16569
<212> TYPE: DNA
<213> ORGANISM: Homo sapiens
<220> FEATURE:
<221> NAME/KEY: misc_feature
<222> LOCATION: (3107)..(3107)
<223> OTHER INFORMATION: n is a, c, g or t

<400> SEQUENCE: 8
gatcacaggt ctatcaccct attaaccact cacgggagct ctccatgcat ttggtatttt        60
cgtctggggg gtatgcacgc gatagcattg cgagacgctg gagccggagc accctatgtc      120
gcagtatctg tctttgattc ctgcctcatc ctattattta tcgcacctac gttcaatatt      180
acaggcgaac atacttacta aagtgtgtta attaattaat gcttgtagga cataataata      240
acaattgaat gtctgcacag ccactttcca cacagacatc ataacaaaaa atttccacca      300
aaccccccct cccccgcttc tggccacagc acttaaacac atctctgcca aaccccaaaa      360
acaaagaacc ctaacaccag cctaaccaga tttcaaattt tatcttttgg cggtatgcac      420
ttttaacagt caccccccaa ctaacacatt attttcccct cccactccca tactactaat      480
ctcatcaata caaccccgc ccatcctacc cagcacacac acaccgctgc taaccccata       540
ccccgaacca accaaacccc aaagacaccc cccacagttt atgtagctta cctcctcaaa      600
gcaatacact gaaaatgttt agacgggctc acatcacccc ataaacaaat aggtttggtc      660
ctagcctttc tattagctct tagtaagatt acacatgcaa gcatcccgt tccagtgagt       720 tcaccctcta atcaccacg atcaaaagga acaagcatca agcacgcagc aatgcagctc       780
aaaacgctta gcctagccac accccacgg gaaacagcag tgattaacct ttagcaataa       840
acgaaagttt aactaagcta tactaacccc agggttggtc aatttcgtgc cagccaccgc      900
ggtcacacga ttaacccaag tcaatagaag ccggcgtaaa gagtgtttta gatcaccccc      960
tccccaataa agctaaaact cacctgagtt gtaaaaaact ccagttgaca caaaatagac     1020
tacgaaagtg ctttaacat atctgaacac acaatagcta agacccaaac tgggattaga     1080
taccccacta tgcttagccc taaacctcaa cagttaaatc aacaaaactg ctcgccagaa     1140
cactacgagc cacagcttaa aactcaaagg acctggcggt gcttcatatc cctctagagg     1200
agcctgttct gtaatcgata aaccccgatc aacctcacca cctcttgctc agcctatata     1260
ccgccatctt cagcaaaccc tgatgaaggc tacaaagtaa gcgcaagtac ccacgtaaag     1320
```

```
acgttaggtc aaggtgtagc ccatgaggtg gcaagaaatg ggctacattt tctacccag      1380 aaaactacga tagcccttat gaaacttaag ggtcgaaggt ggatttagca gtaaactaag     1440
agtagagtgc ttagttgaac agggccctga agcgcgtaca caccgcccgt caccctcctc    1500
aagtatactt caaaggacat ttaactaaaa cccctacgca tttatataga ggagacaagt    1560
cgtaacatgg taagtgtact ggaaagtgca cttggacgaa ccagagtgta gcttaacaca    1620
aagcacccaa cttacactta ggagatttca acttaacttg accgctctga gctaaaccta   1680
gccccaaacc cactccacct tactaccaga caaccttagc caaaccattt acccaaataa    1740
agtataggcg atagaaattg aaacctggcg caatagatat agtaccgcaa gggaaagatg    1800
aaaaattata accaagcata atatagcaag gactaacccc tataccttct gcataatgaa    1860
ttaactagaa ataactttgc aaggagagcc aaagctaaga cccccgaaac cagacgagct    1920
acctaagaac agctaaaaga gcacacccgt ctatgtagca aaatagtggg aagatttata    1980
ggtagaggcg acaaacctac cgagcctggt gatagctggt tgtccaagat agaatcttag    2040 ttcaactttta aatttgccca cagaaccctc taaatcccct tgtaaattta actgttagtc    2100
caaagaggaa cagctctttg gacactagga aaaaaccttg tagagagagt aaaaaattta    2160
acacccatag taggcctaaa agcagccacc aattaagaaa gcgttcaagc tcaacaccca    2220
ctacctaaaa aatcccaaac atataactga actcctcaca cccaattgga ccaatctatc    2280
accctataga agaactaatg ttagtataag taacatgaaa acattctcct ccgcataagc    2340
ctgcgtcaga ttaaaacact gaactgacaa ttaacagccc aatatctaca atcaaccaac    2400
aagtcattat taccctcact gtcaacccaa cacaggcatg ctcataagga aaggttaaaa    2460
aaagtaaaag gaactcggca aatcttaccc cgcctgttta ccaaaaacat cacctctagc    2520
atcaccagta ttagaggcac cgcctgccca gtgacacatg tttaacggcc gcggtaccct    2580
aaccgtgcaa aggtagcata atcacttgtt ccttaaatag ggacctgtat gaatggctcc    2640
acgagggttc agctgtctct tactttttaac cagtgaaatt gacctgcccg tgaagaggcg    2700
ggcataacac agcaagacga gaagacccta tggagcttta atttattaat gcaaacagta    2760
cctaacaaac ccacaggtcc taaactacca aacctgcatt aaaaatttcg gttggggcga    2820
cctcggagca gaacccaacc tccgagcagt acatgctaag acttcaccag tcaaagcgaa    2880
ctactatact caattgatcc aataacttga ccaacggaac aagttaccct agggataaca    2940
gcgcaatcct attctagagt ccatatcaac aataggggttt acgacctcga tgttggatca    3000
ggacatcccg atggtgcagc cgctattaaa ggttcgtttg ttcaacgatt aaagtcctac    3060
gtgatctgag ttcagaccgg agtaatccag gtcggtttct atctacnttc aaattcctcc    3120
ctgtacgaaa ggacaagaga aataaggcct acttcacaaa gcgccttccc ccgtaaatga    3180
tatcatctca acttagtatt atacccacac ccacccaaga acagggtttg ttaagatggc    3240
agagcccggt aatcgcataa aacttaaaac tttacagtca gaggttcaat tcctcttctt    3300
aacaacatac ccatggccaa cctcctactc ctcattgtac ccattctaat cgcaatggca    3360
ttcctaatgc ttaccgaacg aaaaattcta ggctatatac aactacgcaa aggccccaac    3420
gttgtaggcc cctacgggct actacaaccc ttcgctgacg ccataaaact cttcaccaaa    3480
gagcccctaa aaccgccac atctaccatc acccctctaca tcaccgcccc gaccttagct    3540
ctcaccatcg ctcttctact atgaacccccc ctccccatac caaccccct ggtcaacctc    3600 aacctaggcc tcctatttat tctagccacc tctagcctag ccgttactc aatcctctga    3660 tcagggtgag catcaaactc aaactacgcc ctgatcggcg cactgcgagc agtagcccaa    3720
```

```
acaatctcat atgaagtcac cctagccatc attctactat caacattact aataagtggc     3780
tcctttaacc tctccaccct tatcacaaca caagaacacc tctgattact cctgccatca     3840
tgacccttgg ccataatatg atttatctcc acactagcag agaccaaccg aaccccttc      3900 gaccttgccg aaggggagtc cgaactagtc tcaggcttca acatcgaata cgccgcaggc     3960
cccttcgccc tattcttcat agccgaatac acaaacatta ttataataaa caccctcacc     4020
actacaatct tcctaggaac aacatatgac gcactctccc ctgaactcta cacaacatat     4080
tttgtcacca agaccctact tctaacctcc ctgttcttat gaattcgaac agcataccccc    4140 cgattccgct acgaccaact catacacctc ctatgaaaaa acttcctacc actcacccta     4200
gcattactta tatgatatgt ctccataccc attacaatct ccagcattcc ccctcaaacc     4260
taagaaatat gtctgataaa agagttactt tgatagagta aataatagga gcttaaaccc     4320
ccttatttct aggactatga gaatcgaacc catccctgag aatccaaaat tctccgtgcc     4380
acctatcaca ccccatccta agtaaggtc agctaaataa gctatcgggc ccatacccccg     4440 aaaatgttgg ttatacccct cccgtactaa ttaatcccct ggcccaaccc gtcatctact     4500
ctaccatctt tgcaggcaca ctcatcacag cgctaagctc gcactgattt tttacctgag     4560
taggcctaga aataaacatg ctagctttta ttccagttct aaccaaaaaa ataaaccctc     4620
gttccacaga agctgccatc aagtatttcc tcacgcaagc aaccgcatcc ataatccttc     4680
taatagctat cctcttcaac aatatactct ccggacaatg aaccataacc aatactacca     4740
atcaatactc atcattaata atcataatag ctatagcaat aaaactagga atagccccct     4800
ttcacttctg agtcccagag gttacccaag gcacccctct gacatccggc ctgcttcttc     4860
tcacatgaca aaaactagcc cccatctcaa tcatatacca aatctctccc tcactaaacg     4920
taagccttct cctcactctc tcaatcttat ccatcatagc aggcagttga ggtggattaa     4980
accaaaccca gctacgcaaa atcttagcat actcctcaat tacccacata ggatgaataa     5040
tagcagttct accgtacaac cctaacataa ccattcttaa tttaactatt tatattatcc     5100
taactactac cgcattccta ctactcaact aaaactccag caccacgacc ctactactat     5160
ctcgcacctg aaacaagcta acatgactaa caccctaat tccatccacc ctcctctccc      5220
taggaggcct gccccgcta accggctttt tgcccaaatg ggccattatc gaagaattca      5280
caaaaaacaa tagcctcatc atccccacca tcatagccac catcaccctc cttaaccrct     5340
acttctacct acgcctaatc tactccacct caatcacact actccccata tctaacaacg     5400
taaaaataaa atgacagttt gaacatacaa aacccacccc attcctcccc acactcatcg     5460
cccttaccac gctactccta cctatctccc cttttatact aataatctta tagaaattta     5520
ggttaaatac agaccaagag ccttcaaagc cctcagtaag ttgcaatact taatttctgt     5580
aacagctaag gactgcaaaa ccccactctg catcaactga acgcaaatca gccactttaa     5640
ttaagctaag cccttactag accaatggga cttaaaccca caaacactta gttaacagct     5700
aagcacccta atcaactggc ttcaatctac ttctcccgcc gccgggaaaa aaggcgggag     5760
aagccccggc aggtttgaag ctgcttcttc gaatttgcaa ttcaatatga aaatcacctc     5820
ggagctggta aaaagaggcc taaccccctgt ctttagattt acagtccaat gcttcactca     5880
gccattttac ctcacccca ctgatgttcg ccgaccgttg actattctct acaaaccaca     5940
aagacattgg aacactatac ctattattcg gcgcatgagc tggagtccta ggcacagctc     6000
taagcctcct tattcgagcc gagctgggcc agccaggcaa ccttctaggt aacgaccaca     6060
tctacaacgt tatcgtcaca gcccatgcat ttgtaataat cttcttcata gtaatacccca    6120
```

```
tcataatcgg aggctttggc aactgactag ttcccctaat aatcggtgcc cccgatatgg    6180
cgtttccccg cataaacaac ataagcttct gactcttacc tccctctctc ctactcctgc    6240
tcgcatctgc tatagtggag gccggagcag gaacaggttg aacagtctac cctcccttag    6300
cagggaacta ctcccaccct ggagcctccg tagacctaac catcttctcc ttacacctag    6360
caggtgtctc ctctatctta ggggccatca atttcatcac aacaattatc aatataaaac    6420
cccctgccat aacccaatac caaacgcccc tcttcgtctg atccgtccta atcacagcag    6480
tcctacttct cctatctctc ccagtcctag ctgctggcat cactatacta ctaacagacc    6540
gcaacctcaa caccaccttc ttcgaccccg ccggaggagg agaccccatt ctataccaac    6600
acctattctg attttttcggt caccctgaag tttatattct tatcctacca ggcttcggaa    6660
taatctccca tattgtaact tactactccg gaaaaaaaga accatttgga tataggta    6720
tggtctgagc tatgatatca attggcttcc tagggtttat cgtgtgagca caccatatat    6780
ttacagtagg aatagacgta gacacacgag catatttcac ctccgctacc ataatcatcg    6840
ctatcccac cggcgtcaaa gtatttagct gactcgccac actccacgga agcaatatga    6900
aatgatctgc tgcagtgctc tgagccctag gattcatctt tcttttcacc gtaggtggcc    6960
tgactggcat tgtattagca aactcatcac tagacatcgt actacacgac acgtactacg    7020
ttgtagccca cttccactat gtcctatcaa taggagctgt atttgccatc ataggaggct    7080
tcattcactg atttcccta ttctcaggct acacctaga ccaaacctac gccaaaatcc    7140
atttcactat catattcatc ggcgtaaatc taactttctt cccacaacac tttctcggcc    7200
tatccggaat gccccgacgt tactcggact accccgatgc atacaccaca tgaaacatcc    7260
tatcatctgt aggctcattc atttctctaa cagcagtaat attaataatt ttcatgattt    7320
gagaagcctt cgcttcgaag cgaaaagtcc taatagtaga agaaccctcc ataaacctgg    7380
agtgactata tggatgcccc ccacccatacc acacattcga agaaccgtga tacataaaat    7440
ctagacaaaa aaggaaggaa tcgaacccc caaagctggt ttcaagccaa ccccatggcc    7500
tccatgactt tttcaaaaag gtattagaaa aaccatttca taactttgtc aaagttaaat    7560
tataggctaa atcctatata tcttaatggc acatgcagcg caagtaggtc tacaagacgc    7620
tacttcccct atcatagaag agcttatcac cttcatgat cacgccctca taatcatttt    7680
ccttatctgc ttcctagtcc tgtatgccct tttcctaaca ctcacaacaa aactaactaa    7740
tactaacatc tcagacgctc aggaaataga aaccgtctga actatcctgc ccgccatcat    7800
cctagtcctc atcgccctcc catccctacg catcctttac ataacagacg aggtcaacga    7860
tccctccctt accatcaaat caattggcca ccaatggtac tgaacctacg agtacaccga    7920
ctacggcgga ctaatcttca actcctacat acttcccca ttattcctag aaccaggcga    7980
cctgcgactc cttgacgttg acaatcgagt agtactcccg attgaagccc ccattcgtat    8040
aataattaca tcacaagacg tcttgcactc atgagctgtc cccacattag cttaaaaac    8100
agatgcaatt cccggacgtc taaaccaaac cactttcacc gctacacgac cgggggtata    8160
ctacggtcaa tgctctgaaa tctgtggagc aaaccacagt ttcatgccca tcgtcctaga    8220
attaattccc ctaaaatct ttgaaatagg gcccgtattt accctatagc acccctcta    8280
cccctctag agcccactgt aaagctaact tagcattaac ctttaagtt aaagattaag    8340
agaaccaaca cctctttaca gtgaaatgcc ccaactaaat actaccgtat ggcccaccat    8400
aattccccc atactcctta cactattcct catcacccaa ctaaaatat aaacacaaa    8460
ctaccaccta cctccctcac caaagcccat aaaaataaaa aattataaca aaccctgaga    8520
```

```
accaaaatga acgaaaatct gttcgcttca ttcattgccc ccacaatcct aggcctaccc    8580
gccgcagtac tgatcattct atttcccct ctattgatcc ccacctccaa atatctcatc    8640
aacaaccgac taatcaccac ccaacaatga ctaatcaaac taacctcaaa acaaatgata    8700
accatacaca acactaaagg acgaacctga tctcttatac tagtatccct aatcattttt    8760
attgccacaa ctaacctcct cggactcctg cctcactcat ttacaccaac cacccaacta    8820
tctataaacc tagccatggc catccccta tgagcgggca cagtgattat aggctttcgc    8880
tctaagatta aaaatgccct agcccacttc ttaccacaag gcacacctac acccttatc    8940 cccatactag ttattatcga aaccatcagc ctactcattc aaccaatagc cctggccgta    9000
cgcctaaccg ctaacattac tgcaggccac ctactcatgc acctaattgg aagcgccacc    9060
ctagcaatat caaccattaa ccttccctct acacttatca tcttcacaat tctaattcta    9120
ctgactatcc tagaaatcgc tgtcgcctta atccaagcct acgttttcac acttctagta    9180
agcctctacc tgcacgacaa cacataatga cccaccaatc acatgcctat catatagtaa    9240
aacccagccc atgaccccta acaggggccc tctcagccct cctaatgacc tccggcctag    9300
ccatgtgatt tcacttccac tccataacgc tcctcatact aggcctacta accaacacac    9360
taaccatata ccaatgatgg cgcgatgtaa cacgagaaag cacataccaa ggccaccaca    9420
caccacctgt ccaaaaaggc cttcgatacg ggataatcct atttattacc tcagaagttt    9480
ttttcttcgc aggatttttc tgagcctttt accactccag cctagcccct accccccaat    9540
taggagggca ctggcccccca acaggcatca ccccgctaaa tcccctagaa gtcccactcc    9600
taaacacatc cgtattactc gcatcaggag tatcaatcac ctgagctcac catagtctaa    9660
tagaaaacaa ccgaaaccaa ataattcaag cactgcttat tacaatttta ctgggtctct    9720 atttaccct cctacaagcc tcagagtact tcgagtctcc cttcaccatt tccgacggca    9780
tctacggctc aacattttt gtagccacag gcttccacgg acttcacgtc attattggct    9840
caactttcct cactatctgc ttcatccgcc aactaatatt tcactttaca tccaaacatc    9900
actttggctt cgaagccgcc gcctgatact ggcattttgt agatgtggtt tgactatttc    9960
tgtatgtctc catctattga tgagggtctt actcttttag tataaatagt accgttaact    10020
tccaattaac tagttttgac aacattcaaa aaagagtaat aaacttcgcc ttaattttaa    10080
taatcaacac cctcctagcc ttactactaa taattattac attttgacta ccacaactca    10140
acggctacat agaaaaatcc accccttacg agtgcggctt cgaccctata tccccgccc    10200 gcgtcccttt ctccataaaa ttcttcttag tagctattac cttcttatta tttgatctag    10260
aaattgccct ccttttaccc ctaccatgag ccctacaaac aactaacctg ccactaatag    10320
ttatgtcatc cctcttatta atcatcatcc tagccctaag tctggcctat gagtgactac    10380
aaaaaggatt agactgaacc gaattggtat atagtttaaa caaaacgaat gatttcgact    10440
cattaaatta tgataatcat atttaccaaa tgcccctcat ttacataaat attatactag    10500
catttaccat ctcacttcta ggaatactag tatatcgctc acacctcata tcctccctac    10560
tatgcctaga aggaataata ctatcgctgt tcattatagc tactctcata accctcaaca    10620
cccactccct cttagccaat attgtgccta ttgccatact agtctttgcc gctgcgaag    10680 cagcggtggg cctagcccta ctagtctcaa tctccaacac atatggccta gactacgtac    10740
ataacctaaa cctactccaa tgctaaaact aatcgtccca acaattatat tactaccact    10800
gacatgactt tccaaaaaac acataatttg aatcaacaca accacccaca gcctaattat    10860
tagcatcatc cctctactat ttttaacca aatcaacaac aacctattta gctgttcccc    10920
```

-continued

```
aaccttttcc tccgacccccc taacaaccccc cctcctaata ctaactacct gactcctacc   10980
cctcacaatc atggcaagcc aacgccactt atccagtgaa ccactatcac gaaaaaaact   11040
ctacctctct atactaatct ccctacaaat ctccttaatt ataacattca cagccacaga   11100
actaatcata ttttatatct tcttcgaaac cacacttatc cccaccttgg ctatcatcac   11160
ccgatgaggc aaccagccag aacgcctgaa cgcaggcaca tacttcctat tctacaccct   11220
agtaggctcc cttcccctac tcatcgcact aatttacact cacaacaccc taggctcact   11280
aaacattcta ctactcactc tcactgccca agaactatca aactcctgag ccaacaactt   11340
aatatgacta gcttacacaa tagctttat agtaaagata cctctttacg gactccactt   11400
atgactccct aaagcccatg tcgaagcccc catcgctggg tcaatagtac ttgccgcagt   11460
actcttaaaa ctaggcggct atggtataat acgcctcaca ctcattctca accccctgac   11520
aaaacacata gcctacccct tccttgtact atccctatga ggcataatta taacaagctc   11580
catctgccta cgacaaacag acctaaaatc gctcattgca tactcttcaa tcagccacat   11640
agccctcgta gtaacagcca ttctcatcca acccccctga agcttcaccg cgcagtcat   11700
tctcataatc gcccacgggc ttacatcctc attactattc tgcctagcaa actcaaacta   11760
cgaacgcact cacagtcgca tcataatcct ctctcaagga cttcaaactc tactcccact   11820
aatagcttt tgatgacttc tagcaagcct cgctaacctc gccttacccc ccactattaa   11880
cctactggga gaactctctg tgctagtaac cacgttctcc tgatcaaata tcactctcct   11940
acttacagga ctcaacatac tagtcacagc cctatactcc ctctacatat ttaccacaac   12000
acaatggggc tcactcaccc accacattaa caacataaaa ccctcattca cacgagaaaa   12060
caccctcatg ttcatacacc tatcccccat tctcctccta tccctcaacc ccgacatcat   12120
taccgggttt tcctcttgta atatagtttt aaccaaaaca tcagattgtg aatctgacaa   12180
cagaggctta cgacccctta tttaccgaga agctcacaa gaactgctaa ctcatgcccc   12240
catgtctaac aacatggctt tctcaacttt taaaggataa cagctatcca ttggtcttag   12300
gccccaaaaa ttttggtgca actccaaata aaagtaataa ccatgcacac tactataacc   12360
accctaacccc tgacttccct aattcccccc atccttacca ccctcgttaa ccctaacaaa   12420
aaaaactcat acccccatta tgtaaaatcc attgtcgcat ccacctttat tatcagtctc   12480
ttccccacaa caatattcat gtgcctagac caagaagtta ttatctcgaa ctgacactga   12540
gccacaaccc aaacaaccca gctctcccta agcttcaaac tagactactt ctccataata   12600
ttcatccctg tagcattgtt cgttacatgg tccatcatag aattctcact gtgatatata   12660
aactcagacc caaacattaa tcagttcttc aaatatctac tcatcttcct aattaccata   12720
ctaatcttag ttaccgctaa caacctattc caactgttca tcggctgaga gggcgtagga   12780
attatatcct tcttgctcat cagttgatga tacgcccgag cagatgccaa cacagcagcc   12840
attcaagcaa tcctatacaa ccgtatcggc gatatcggtt tcatcctcgc cttagcatga   12900
tttatcctac actccaactc atgagaccca caacaaatag cccttctaaa cgctaatcca   12960
agcctcaccc cactactagg cctcctccta gcagcagcag gcaaatcagc ccaattaggt   13020
ctccacccct gactccccctc agccatagaa ggccccaccc cagtctcagc cctactccac   13080
tcaagcacta tagttgtagc aggaatcttc ttactcatcc gcttccaccc cctagcagaa   13140
aatagcccac taatccaaac tctaacacta tgcttaggcg ctatcaccac tctgttcgca   13200
gcagtctgcg cccttacaca aaatgacatc aaaaaaatcg tagccttctc cacttcaagt   13260
caactaggac tcataatagt tacaatcggc atcaaccaac cacacctagc attcctgcac   13320
```

```
atctgtaccc acgccttctt caaagccata ctatttatgt gctccgggtc catcatccac   13380
aaccttaaca atgaacaaga tattcgaaaa ataggaggac tactcaaaac catacctctc   13440
acttcaacct ccctcaccat tggcagccta gcattagcag gaatacccttt cctcacaggt  13500 ttctactcca aagaccacat catcgaaacc gcaaacatat catacacaaa cgcctgagcc   13560
ctatctatta ctctcatcgc tacctccctg acaagcgcct atagcactcg aataattctt   13620
ctcaccctaa caggtcaacc tcgcttcccc acccttacta acattaacga aaataacccc   13680
accctactaa accccattaa acgcctggca gccggaagcc tattcgcagg atttctcatt   13740
actaacaaca tttcccccgc atcccccttc caaacaacaa tccccctcta cctaaaactc   13800
acagccctcg ctgtcacttt cctaggactt ctaacagccc tagacctcaa ctacctaacc   13860
aacaaactta aaataaaatc cccactatgc acatttttatt tctccaacat actcggattc   13920
taccctagca tcacacaccg cacaatcccc tatctaggcc ttcttacgag ccaaaacctg   13980
cccctactcc tcctagacct aacctgacta gaaaagctat tacctaaaac aatttcacag   14040
caccaaatct ccacctccat catcacctca acccaaaaag gcataattaa actttacttc   14100
ctctctttct tcttcccact catcctaacc ctactcctaa tcacataacc tattcccccg   14160
agcaatctca attacaatat atacaccaac aaacaatgtt caaccagtaa ctactactaa   14220
tcaacgccca taatcataca aagcccccgc accaatagga tcctcccgaa tcaaccctga   14280
cccctctcct tcataaatta ttcagcttcc tacactatta aagttaccca aaccaccac    14340 cccatcatac tctttcaccc acagcaccaa tcctacctcc atcgctaacc ccactaaaac   14400
actcaccaag acctcaaccc ctgacccccca tgcctcagga tactcctcaa tagccatcgc   14460
tgtagtatat ccaaagacaa ccatcattcc ccctaaataa attaaaaaaa ctattaaacc   14520
catataacct cccccaaaat tcagaataat aacacacccg accacaccgc taacaatcaa   14580
tactaaaccc ccataaatag gagaaggctt agaagaaaac cccacaaacc ccattactaa   14640
acccacactc aacagaaaca aagcatacat cattattctc gcacggacta caaccacgac   14700
caatgatatg aaaaaccatc gttgtatttc aactacaaga acaccaatga ccccaatacg   14760
caaaactaac cccctaataa aattaattaa ccactcattc atcgacctcc caccccatc    14820 caacatctcc gcatgatgaa acttcggctc actccttggc gcctgcctga tcctccaaat   14880
caccacagga ctattcctag ccatgcacta ctcaccagac gcctcaaccg cctttttcatc   14940 aatcgcccac atcactcgag acgtaaatta tggctgaatc atccgctacc ttcacgccaa   15000
tggcgcctca atattcttta tctgcctctt cctacacatc gggcgaggcc tatattacgg   15060
atcatttctc tactcagaaa cctgaaacat cggcattatc ctcctgcttg caactatagc   15120
aacagccttc ataggctatg tcctcccgtg aggccaaata tcattctgag gggccacagt   15180
aattacaaac ttactatccg ccatcccata cattgggaca gacctagttc aatgaatctg   15240
aggaggctac tcagtagaca gtcccaccct cacacgattc tttacctttc acttcatctt   15300
gcccttcatt attgcagccc tagcaacact ccacctccta ttcttgcacg aaacgggatc   15360
aaacaacccc ctaggaatca cctcccattc cgataaaatc accttccacc cttactacac   15420
aatcaaagac gccctcggct tacttctctt ccttctctcc ttaatgacat taacactatt   15480
ctcaccagac ctcctaggcg acccagacaa ttatacccta gccaaccccct taaacacccc   15540 tccccacatc aagcccgaat gatatttcct attcgcctac acaattctcc gatccgtccc   15600
taacaaacta ggaggcgtcc ttgccctatt actatccatc ctcatcctag caataatccc   15660
catcctccat atatccaaac aacaaagcat aatatttcgc ccactaagcc aatcacttta   15720
```

```
ttgactccta gccgcagacc tcctcattct aacctgaatc ggaggacaac cagtaagcta    15780
cccttttacc atcattggac aagtagcatc cgtactatac ttcacaacaa tcctaatcct    15840
aataccaact atctccctaa ttgaaaacaa aatactcaaa tgggcctgtc cttgtagtat    15900
aaactaatac accagtcttg taaaccggag atgaaaacct ttttccaagg acaaatcaga    15960
gaaaaagtct ttaactccac cattagcacc caaagctaag attctaattt aaactattct    16020
ctgttctttc atggggaagc agatttgggt accaccaag tattgactca cccatcaaca     16080
accgctatgt atttcgtaca ttactgccag ccaccatgaa tattgtacgg taccataaat    16140
acttgaccac ctgtagtaca taaaaaccca atccacatca aaacccctc cccatgctta     16200 caagcaagta cagcaatcaa ccctcaacta tcacacatca actgcaactc caaagccacc    16260
cctcacccac taggatacca acaaacctac ccacccttaa cagtacatag tacataaagc    16320
catttaccgt acatagcaca ttacagtcaa atcccttctc gtccccatgg atgacccccc    16380
tcagataggg gtcccttgac caccatcctc cgtgaaatca atatcccgca caagagtgct    16440
actctcctcg ctccgggccc ataacacttg ggggtagcta aagtgaactg tatccgacat    16500
ctggttccta cttcagggtc ataaagccta aatagcccac acgttcccct taaataagac    16560
atcacgatg                                                            16569

<210> SEQ ID NO 9
<211> LENGTH: 22
<212> TYPE: DNA
<213> ORGANISM: Artificial Sequence
<220> FEATURE:
<223> OTHER INFORMATION: synthetic primer forward 3.4 kb deleted
      sequence

<400> SEQUENCE: 9
cccactcatc acctaaacct ac                                                 22

<210> SEQ ID NO 10
<211> LENGTH: 20
<212> TYPE: DNA
<213> ORGANISM: Artificial Sequence
<220> FEATURE:
<223> OTHER INFORMATION: synthetic primer reverse 3.4 kb deleted
      sequence

<400> SEQUENCE: 10
ggtaggagtc aggtagttag                                                    20
```

3.4 KB MITOCHONDRIAL DNA DELETION FOR USE IN THE DETECTION OF CANCER

CROSS REFERENCE TO RELATED APPLICATIONS

This application is a continuation of U.S. patent application Ser. No. 15/470,175, filed Mar. 27, 2017, which is a continuation of U.S. patent application Ser. No. 14/874,155, filed Oct. 2, 2015, which is a continuation of U.S. patent application Ser. No. 14/507,027, filed Oct. 6, 2014, which is a continuation of U.S. patent application Ser. No. 12/748,120, filed Mar. 26, 2010, which is a continuation-in-part of U.S. patent application Ser. No. 11/975,390, filed Oct. 18, 2007, now U.S. Pat. No. 8,008,008 issued Aug. 30, 2011, which is a continuation of PCT/CA2006/000652, filed Apr. 18, 2006, which PCT application claims the benefit under 35 U.S.C. § 119(e) of U.S. Provisional Patent Application Nos. 60/672,016, filed Apr. 18, 2005; 60/721,522, filed Sep. 29, 2005; and 60/789,872, filed Apr. 7, 2006, which applications are hereby incorporated by reference in their entireties. Additionally, this application is a continuation of U.S. patent application Ser. No. 15/470,175, filed Mar. 27, 2017, which is a continuation of U.S. patent application Ser. No. 14/874, 155, filed Oct. 2, 2015, which is a continuation of U.S. patent application Ser. No. 14/507,027 filed Oct. 6, 2014 which is a continuation of U.S. patent application Ser. No. 12/748,120, filed Mar. 26, 2010, which is a continuation of PCT/CA2007/001711, filed Sep. 26, 2007, which applications are hereby incorporated by reference in their entireties.

REFERENCE TO SEQUENCE IDENTIFICATION LISTING

The present application includes a sequence identification listing in .txt format as follows:
Filename: Sequence_Listing.txt
Size: 28 KB
Date Created: Jun. 1, 2019
This sequence identification listing is hereby expressly incorporated by reference in its entirety in the present application.

FIELD OF THE INVENTION

This invention is related to the field of mitochondrial genomics. In particular it is related to a 3.4 kb deletion in the mitochondrial genome and its utility as an indicator of cancer.

BACKGROUND OF THE INVENTION

Mitochondrial DNA (MtDNA) as a Diagnostic Tool

MtDNA sequence dynamics are important diagnostic tools. Mutations in mtDNA are often preliminary indicators of developing disease, often associated with nuclear mutations, and act as biomarkers specifically related to: disease, such as but not limited to, tissue damage and cancer from smoking and exposure to second hand tobacco smoke (Lee et al., 1998; Wei, 1998); longevity, based on accumulation of mitochondrial genome mutations beginning around 20 years of age and increasing thereafter (von Wurmb, 1998); metastatic disease caused by mutation or exposure to carcinogens, mutagens, ultraviolet radiation (Birch-Machin, 2000); osteoarthritis; cardiovascular, Alzheimer, Parkinson disease (Shoffner et al., 1993; Sherratt et al., 1997; Zhang et al, 1998); age associated hearing loss (Seidman et al., 1997); optic nerve degeneration and cardiac dysrhythmia (Brown et al., 1997; Wallace et al., 1988); chronic progressive external exophthalmoplegia (Taniike et al., 1992); atherosclerosis (Bogliolo et al., 1999); papillary thyroid carcinomas and thyroid tumours (Yeh et al., 2000); as well as others (e.g. Naviaux, 1997; Chinnery and Turnbull, 1999).

Mutations at specific sites of the mitochondrial genome can be associated with certain diseases. For example, mutations at positions 4216, 4217 and 4917 are associated with Leber's Hereditary Optic Neuropathy (LHON) (Mitochondrial Research Society; Huoponen (2001); MitoMap). A mutation at 15452 was found in 5/5 patients to be associated with ubiquinol cytochrome c reductase (complex III) deficiency (Valnot et al. 1999).

Specifically, these mutations or alterations include point mutations (transitions, transversions), deletions (one base to thousands of bases), inversions, duplications, (one base to thousands of bases), recombinations and insertions (one base to thousands of bases). In addition, specific base pair alterations, deletions, or combinations thereof have been found to be associated with early onset of prostate, skin, and lung cancer, as well as aging (e.g. Polyak et al., 1998), premature aging, exposure to carcinogens (Lee et al., 1998), etc.

Prostate Cancer

Prostate cancer is a frequently diagnosed solid tumour that most likely originates in the prostate epithelium (Huang et al. 1999). In 1997, nearly 10 million American men were screened for prostate specific antigen (PSA), the presence of which suggests prostate cancer (Woodwell, 1999). Indeed, this indicates an even higher number of men screened by an initial digital rectal exam (DRE). In the same year, 31 million men had a DRE (Woodwell, 1999). Moreover, the annual number of newly diagnosed cases of prostate cancer in the United States is estimated at 179,000 (Landis et al., 1999). It is the second most commonly diagnosed cancer and second leading cause of cancer mortality in Canadian men. In 1997 prostate cancer accounted for 19,800 of newly diagnosed cancers in Canadian men (28%) (National Cancer Institute of Canada). It is estimated that 30% to 40% of all men over the age of forty-nine (49) have some cancerous prostate cells, yet only 20% to 25% of these men have a clinically significant form of prostate cancer (SpringNet-CE Connection, internet, www.springnet.com/ce/j803a.htm). Prostate cancer exhibits a wide variety of histological behaviour involving both endogenous and exogenous factors, i.e. socio-economic situations, diet, geography, hormonal imbalance, family history and genetic constitution (Konishi et al. 1997; Hayward et al. 1998). Although certain mtDNA alterations have been previously associated with prostate cancer, the need exists for further markers for the detection of prostate cancer.

3.4 kb mtDNA Deletion and the Detection of Prostate Cancer.

In the applicant's pending PCT application bearing publication no. WO/06/111029 (the entire contents of which are incorporated herein by reference) a deletion of a 3379 bp segment of mtDNA was identified through full mitochondrial genome amplification of prostate tissue. The 3379 bp deletion (referred to as the 3.4 kb deletion) was determined to be spanning nucleotides 10744-14124 of the mitochondrial genome. It was determined that the detection of this deletion could be used in the diagnosis of prostrate cancer when tissue samples are tested.

The 3.4 kb deletion removes all or part of the following genes from the mtDNA genome: (i) NADH dehydrogenase subunit 4L, (ii) NADH dehydrogenase subunit 4, (iii)

NADH dehydrogenase subunit 5, (iv) tRNA histidine, (v) tRNA serine2, and (vi) tRNA leucine2.

Breast Cancer

Breast cancer is a cancer of the glandular breast tissue and is the fifth most common cause of cancer death. In 2005, breast cancer caused 502,000 deaths (7% of cancer deaths; almost 1% of all deaths) worldwide (World Health Organization Cancer Fact Sheet No. 297). Among women worldwide, breast cancer is the most common cancer and the most common cause of cancer death (World Health Organization Cancer Fact Sheet No. 297). Although certain mtDNA alterations have been previously associated with breast cancer, for example, in Parrella et al. (Cancer Research: 61, 2001), the need exists for further markers for the detection of breast cancer.

BRIEF SUMMARY OF THE INVENTION

In one embodiment, the present invention provides a method of detecting a cancer in an individual comprising;
 a) obtaining a biological sample from the individual;
 b) extracting mitochondrial DNA, mtDNA, from the sample;
 c) quantifying the amount of mtDNA in the sample having a deletion in the nucleic acid sequence spanning approximately residues 10744 and 14124 of the mtDNA genome;
 d) comparing the amount of mtDNA in the sample having the deletion to at least one known reference value.

In one embodiment, the present invention provides a method of detecting a cancer in an individual comprising;
 a) obtaining a biological sample from the individual;
 b) extracting mitochondrial DNA, mtDNA, from the sample;
 c) quantifying the amount of mtDNA in the sample having a deletion in the nucleic acid sequence spanning approximately residues 10744 and 14124 of the mtDNA genome;
 d) comparing the amount of mtDNA in the sample having the deletion to the amount of the deletion in a reference sample of mtDNA from known non-cancerous tissue or body fluid;
 wherein an elevated amount of the deletion in the biological sample compared to the reference sample is indicative of cancer.

In one embodiment, the present invention provides a method of detecting a cancer in an individual comprising;
 a) obtaining a biological sample from the individual;
 b) extracting mitochondrial DNA, mtDNA, from the sample;
 c) quantifying the amount of mtDNA in the sample having a deletion in the nucleic acid sequence spanning approximately residues 10744 and 14124 of the mtDNA genome;
 d) comparing the amount of mtDNA in the sample having the deletion to the amount of the deletion in a reference sample of mtDNA from known cancerous tissue or body fluid;
 wherein a similar level of the deletion in the biological sample compared to the reference sample is indicative of cancer.

In one embodiment, the present invention provides a method of monitoring an individual for the development of a cancer comprising;
 a) obtaining a biological sample;
 b) extracting mtDNA from the sample;
 c) quantifying the amount of mtDNA in the sample having a deletion in the nucleic acid sequence spanning approximately residues 10744 and 14124 of the mtDNA genome;
 d) repeating steps a) to c) over a duration of time;
 e) wherein an increasing level of the deletion over the duration of time is indicative of cancer.

In one embodiment, the present invention provides a method of detecting a cancer in an individual comprising;
 a) obtaining a biological sample from the individual;
 b) extracting mitochondrial DNA, mtDNA, from the sample;
 c) quantifying the amount of mtDNA in the sample having a sequence corresponding to the sequence identified in SEQ ID NO: 1;
 d) comparing the amount of mtDNA in the sample corresponding to SEQ ID NO: 1 to at least one known reference value.

BRIEF DESCRIPTION OF THE SEVERAL VIEWS OF THE DRAWINGS

An embodiment of the invention will now be described by way of example only with reference to the appended drawings wherein.

DETAILED DESCRIPTION OF THE INVENTION

Figure 1:
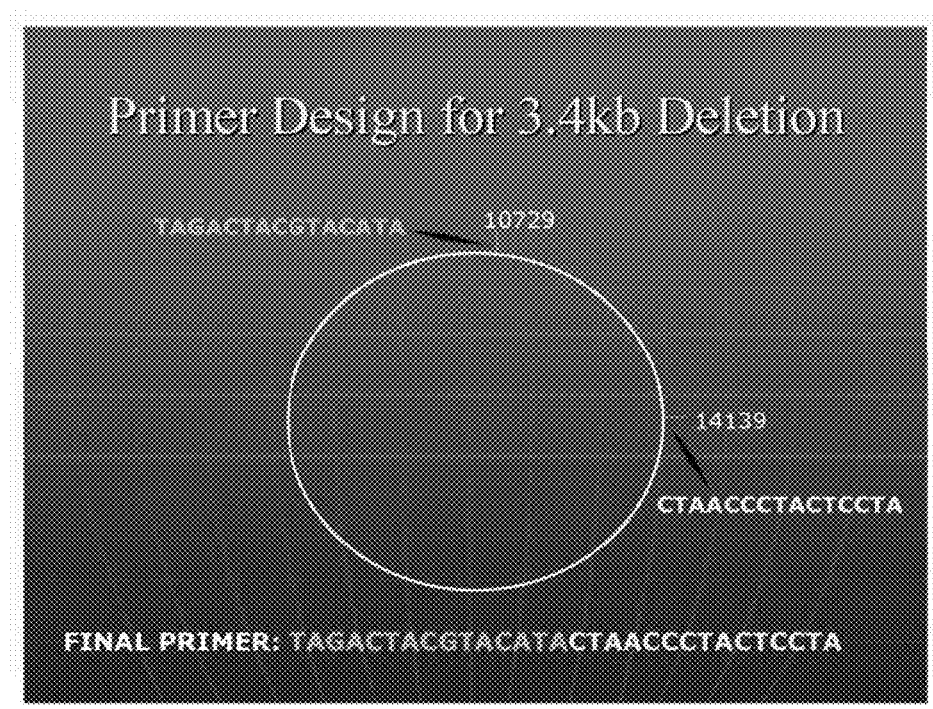
FIG. 1 is a schematic diagram showing the design and sequence of a primer useful for the detection of the 3.4 kb deletion. The primer (SEQ ID NO: 2) binds to bases 10729-10743/14125-14139 of the mtDNA genome, wherein the portion of the primer that binds to bases 10729-10743 is depicted in gray in the upper left corner of the figure (nucleotides 1-15 of SEQ ID NO: 2) and the portion of the primer that binds to bases 14125-14139 is depicted in white in the lower right corner of the figure (nucleotides 16-30 of SEQ ID NO: 2)

As used herein, "cycle threshold" ($C_T$) is the point at which target amplification using real-time PCR rises above background, as indicated by a signal such as a fluorescence signal. The $C_T$ is inversely related to the quantity of the sequence being investigated.

As defined herein, "sensitivity" refers to the fraction of true positives (true positive rate) results obtained using the method of the present invention.

As defined herein, "specificity" refers to the fraction of false positives (false positive rate) results obtained using the method of the present invention.

In one embodiment of the present invention, methods are provided for monitoring and diagnosing cancer through the detection and quantification of the aforementioned 3.4 kb mtDNA deletion. For example, the present invention may be used for detecting the presence of pre-neoplasia, neoplasia and progression towards potential malignancy of prostate cancer and breast cancer. In one aspect, the present invention involves the detection and quantification of the 3.4 kb mtDNA deletion (SEQ ID NO:1) for the detection, diagnosis, and/or monitoring of cancer. In this method, mtDNA is extracted from a biological sample (for example body tissue, or body fluids such as urine, prostate massage fluid). The extracted mtDNA is then tested in order to determine the levels (i.e. quantity) of the 3.4 kb deletion in the sample. In tests conducted by the present inventors, the levels of the deletion were found to be elevated in samples obtained from subjects with cancer when compared to samples obtained from subjects without cancer. Based on the information and data supplied below, the inventors have concluded that elevated levels of the 3.4 kb deletion in the mtDNA is indicative of cancer.

As disclosed in PCT WO/06/111029, the 3.4 kb deletion spans approximately nucleotides 10744 to 14124 of the mtDNA genome. The mtDNA genome is listed as SEQ ID NO:8 (Genbank accession no. AC_000021). The inventors have determined, as provided by example below, that this deletion is also associated with cancer and in particular prostate and breast cancer. Therefore, such deletion provides an accurate biomarker and, therefore, a valuable tool for the detection, diagnosis, or monitoring of cancer in at least these tissues.

The deletion results in the creation of two deletion monomers, one of 3.4 kb in size (small sublimon) and one of approximately 12.6 kb in size (large sublimon). The occurrence of the deletion may be detected by either identifying the presence of the small sublimon, or by determining that the 3.4 kb sequence has been deleted from the large sublimon.

As discussed above, the deletion is approximately 3379 bp, and comprises genes encoding NADH dehydrogenase subunit 4L, NADH dehydrogenase subunit 4, NADH dehydrogenase subunit 5, tRNA histidine, tRNAserine2, and tRNA leucine2.

In one embodiment, samples of, for example prostate tissue, prostate massage fluid, urine or breast tissue, are obtained from an individual and tested over a period of time (e.g. years) in order to monitor the genesis or progression of cancer. Increasing levels of the 3.4 kb deletion over time could be indicative of the beginning or progression of cancer.

Age related accumulation of the 3.4 kb mtDNA deletion may predispose an individual to, for example, prostate cancer or breast cancer, which is prevalent in middle aged and older men, and middle aged and older women, respectively. According to one aspect of the invention, a method is provided wherein regular cancer screening may take place by monitoring over time the amount of the 3.4 kb deletion in body tissues such as breast tissue or body fluids such as prostate massage fluid, or urine.

The system and method of the present invention may be used to detect cancer at an early stage, and before any histological abnormalities. For example, the system and method of the present invention may be used to detect pre-neoplasia in breast tissue.

The following primer sequences are preferred for the detection of the 3.4 kb deletion:

```
3.4 forward (binds to bases 10729-10743/14125-
14139 of the mtDNA genome)
                                        (SEQ ID NO: 2)
5'-TAGACTACGTACATACTAACCCTACTCCTA-3';

3.4 reverse (binds to bases 14361-14379 of the
mtDNA genome)
                                        (SEQ ID NO: 3)
5'-GAGGTAGGATTGGTGCTGT-3'.
```

In one embodiment of the present invention, a pair of amplification primers are used to amplify a target region indicative of the presence of the 3.4 kb deletion. In this embodiment, one of the pair of amplification primers overlaps a spliced region of mtDNA after deletion of the 3.4 kb sequence has occurred (i.e. a splice at a position spanning approximately residues 10744 and 14124 of the mtDNA genome). Therefore, extension of the overlapping primer can only occur if the 3.4 kb section is deleted.

In another embodiment of the present invention, a pair of amplification primers are used to amplify a target region associated with the deleted 3.4 kb sequence. The deleted 3.4 kb sequence, upon deletion, may reform as a circular mtDNA molecule. In this embodiment, one of the pair of amplification primers overlaps the rejoining site of the ends of the 3.4 kb sequence. Thus, an increase in the amount of the 3.4 kb molecule detected in a sample is indicative of cancer. The below primer pair is preferred for the detection of the deleted 3.4 kb nucleic acid.

```
Forward 14115/10755
                                        (SEQ ID NO: 9)
5'-CCCACTCATCACCTAAACCTAC-3'

Reverse 10980R
                                        (SEQ ID NO: 10)
5'-GGTAGGAGTCAGGTAGTTAG-3'.
```

In one aspect of the invention, a kit for diagnosing cancer, for example prostate or breast cancer, comprising means for extraction of mtDNA, primers having the nucleic acid sequences recited in SEQ ID NOS: 2 and 3, or SEQ ID NOS: 9 and 10, reagents and instructions, is provided.

Another aspect of the invention provides methods for confirming or refuting the presence of a cancer biopsy test from a biopsy sample (e.g. prostate or breast cancer), comprising: obtaining non-cancerous tissue from a biopsy sample; and detecting and quantifying the amount of the 3.4 kb mtDNA deletion in the non-diseased tissue.

In one embodiment the present invention provides a method for screening individuals for prostate or breast cancer from a body fluid sample comprising; obtaining a body fluid sample, and detecting and quantifying the level of the 3.4 kb mtDNA deletion in the body fluid.

Although real-time quantitative PCR methods, as described in the examples below, represent the preferred means for detecting and quantifying the presence or absence of the 3.4 kb deletion, other methods that would be well known to an individual of skill in the art could also be utilized. For example quantification of the deletion could be made using Bio-Rad's Bioplex™ System and Suspension Array technology. Generally, the method requires amplification and quantification of sequences using any known methods.

The examples provided below illustrate that not only can this deletion be used for the detection of prostate cancer in prostate tissue, but can also be used to detect the presence of cancer in other biological samples, for example prostate massage fluid, urine, and breast tissue. Based on the findings in these examples, the 3.4 kb mtDNA deletion may be used as a biomarker for cancer.

The various examples provided illustrate a difference in the amount of mtDNA having the 3.4 kb deletion between samples obtained from subjects having cancer, and subjects without cancer. The amount of the 3.4 kb deletion was found to be higher in the samples obtained from subjects having cancer. This determination was made by comparing the amount of the 3.4 kb deletion in the test samples with amounts from known cancer cells and/or known non-cancer cells.

EXAMPLE 1

3.4 kb Deletion in the mtDNA of Prostate Tissue

A deletion of approximately 3.4 kilobases (kb) was identified through full mitochondrial genome amplification of fresh frozen prostate tissue. Using linear regression, the size of the deletion was estimated to be between 3000 base pairs (bp) and 3500 bp. Two possible candidate deletions were identified using Mitomap™ (Brandon, M. C., Lott, M. T., Nguyen, K. C., Spolim, S., Navathe, S. B., Baldi, P. & Wallace, D. C., MITOMAP: a human mitochondrial genome database—2004 update. Nucleic Acids Research 33 (Database Issue):D611-613, 2005; www.mitomap.org.), the 3397 bp deletion at 9574-12972, and the 3379 bp deletion at 10744-14124. In order to determine which of the two deletions was associated with prostate cancer, if either, a forward primer which bridged the deletion junction was developed for each of the two candidates, ensuring that the primer extended further than the repeat regions that flank the deletions. FIG. 1 is a schematic diagram showing the design and sequence of the primer (i.e. SEQ ID NO: 2). Positive amplification results for the amplicon corresponding to the 3379 bp deletion (referred to as the 3.4 kb deletion) at 10744-14124 were obtained.

As indicated above, the 3.4 kb deletion removes all or part of the following genes: (i) NADH dehydrogenase subunit 4L, (ii) NADH dehydrogenase subunit 4, (iii) NADH dehydrogenase subunit 5, (iv) tRNA histidine, (v) tRNA serine2, and (vi) tRNA leucine2.

The 3.4 kb deletion was determined to be present in 91% of 33 fresh frozen prostate samples. With the specific deletion primers, formalin fixed tissues were tested in order increase the n value.

The present investigators sequenced entire mitochondrial genomes from 32 tissue samples microdissected by laser capture microdisection and 12 needle biopsies from histologically normal prostates. Archived tissue sections from each of these samples were used for the following study. 1-2 serial sections were removed from each sample. DNA was extracted from each sample in its entirety rather than as a microdissection. Thus, each sample consisted of a mixture of glandular prostate tissue as well as stromal prostate tissue. This extraction was performed using Qiagen's QIAamp™ DNA Mini Kit (Cat #51304). Following extraction the samples were quantified using a Nano-Drop™ spectrophotometer and the concentrations were subsequently normalized to 2 ng/ul. Each sample was amplified using 20 ng input DNA and an iQ™ SYBR Green Supermix™ kit (Bio-Rad Laboratories Inc.) Reactions were run on an Opticon® 2 two colour real-time PCR system (MJ Research).

Figure 2:
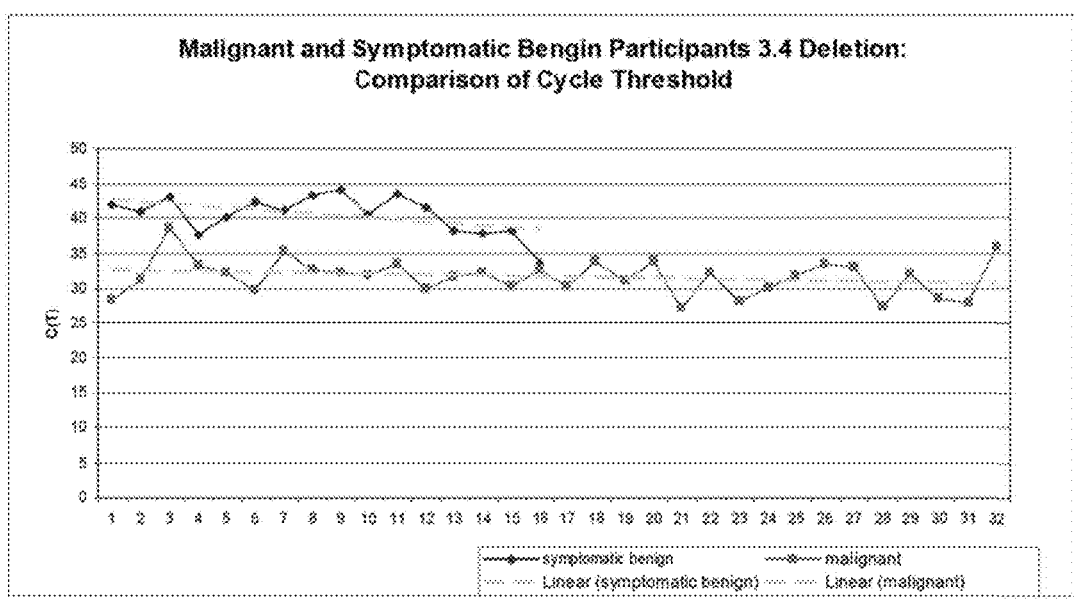
FIG. 2 is a graph showing a comparison of cycle threshold between malignant and symptomatic benign participants in the 3.4 kb study.

As shown in FIG. 2, a distinct difference was observed in cycle threshold and, by extension, quantity of the deletion between the malignant prostate samples and the symptomatic benign prostate samples. Malignant samples exhibited a consistently earlier cycle threshold than the benign samples.

EXAMPLE 2

3.4 kb Deletion Blinded Study—Comparison of Cycle Threshold

An additional 21 prostate tissue samples were selected, 10 of which were benign and 11 of which were malignant. The pathological status was determined by needle biopsies conducted by a qualified pathologist. The samples were blinded such that the present investigators were unaware of their pathological status when they conducted this test. The present investigators were able to predict pathological status correctly in 81% of the cases by examining the cycle threshold. Of the 4 incorrect calls, two were malignant samples that were determined to be benign and 2 were benign samples that were determined to be malignant. Follow-up clinical information for the 2 individuals in the latter scenario was requested from the physician to determine if they had been diagnosed with prostate cancer subsequent to the needle biopsy results used for this study. One of the individuals who originally produced a benign sample but was predicted by this study to have a malignancy subsequently produced a malignant sample. As a result, one of the false positives became a true positive. Therefore, pathological status was predicted correctly in 86% of the cases examined in this study. The ultimate positive predictive value (PPV, where PPV=true positives/(true positives+ false positives)) for this study was 91% and the negative predictive value (NPV, where NPV=true negatives/(true negatives+false negatives)) was 80%.

EXAMPLE 3

3.4 kb Deletion Study—Methods (n=76)

Seventy-six prostate tissue samples were examined for the 3.4 kb deletion in this study. All tissue samples were formalin-fixed, 25 being malignant, 12 being normal, and 39 having benign prostatic disease as shown histologically. Of the latter group more then half had hyperplasia. All specimens were needle biopsies taken from the investigators' tissue archives.

Prostate Specimens

A tapelift was performed on each slide using Prep-Strips (Catalogue Number LCM0207) from Arcturus Bioscience Inc. This allowed the removal of any particulate matter or non-adhering tissue from the slide prior to DNA extraction. With the tissue still on the slides, the slides were rinsed with PBS (Phosphate Buffered Saline Solution) to remove as much fixative as possible. The 1-2 needle biopsy sections on the slides were scraped into sterile microcentrifuge tubes using individually wrapped, sterilized surgical razor blades. DNA was then isolated and purified using a QIAamp® DNA Mini Kit (Qiagen, Cat. #51304) according to manufacturer's specifications. A negative extract control was processed in parallel with the slide extractions as a quality control checkpoint. The total concentration of DNA and purity ratio for each sample was determined by spectrophotometry (Nano-Drop™ ND-1000) and dilutions of 2 ng/µl were prepared for the purpose of Quantitative Polymerase Chain Reaction (qPCR).

Primers (Oligonucleotides)

Purified oligonucleotide primers were chemically synthesized by Invitrogen (California, USA). The sequences of the primers and the expected sizes of the PCR products amplified are listed in Table 1. In addition, PCR analysis for mtDNA deletions included positive controls (DNA from a source known to carry the mutant mtDNA). Each primer set with the exception of TNF (tumor necrosis factor) were checked against a mitochondria-free rho 0 cell line to confirm the absence of pseudogene coamplification.

TABLE 1

Amplification Primers.

| Primer Pair | Position Amplified 5'-3' | Length of amplified product (base pairs) |
|---|---|---|
| 3.4 Deletion Real-Time | 10729-14379 (less 3379 bp at 10744-14124) | 273 |
| 12s mtDNA | 708-945 | 238 |
| TNF | 3756-3886 | 131 |

3.4 forward (10729-10743-14125-14139)
5'TAGACTACGTACATACTAACCCTACTCCTA-3' SEQ ID NO: 2

3.4 reverse (14361-14379) 5'-GAGGTAGGATTGGTGCTGT-3' SEQ ID NO: 3

12s forward (708-728) 5'-CGTTCCAGTGAGTTCACCCTC-3' SEQ ID NO: 4

12s reverse (923-945) 5'-CACTCTTTACGCCGGCTTCTATT-3' SEQ ID NO: 5

TNF forward (3756-3775) 5'-CCTGCCCCAATCCCTTTATT-3' SEQ ID NO: 6

TNF reverse (3866-3886) 5'-GGTTTCGAAGTGGTGGTCTTG-3' SEQ ID NO: 7

Real-Time Polymerase Chain Reaction

Three separate PCRs were performed on each sample. Each reaction was 25 µl total volume and included template DNA, one pair of primers (12s or 3.4 Deletion or TNF), an iQ™ SYBR Green Supermix™ kit (Catalogue Number 170-8882, Bio-Rad Laboratories Inc.) and distilled deionized water (ddH$_2$O). The TNF (tumor necrosis factor) comprised single copy nuclear gene primers, and 12s comprised total mitochondrial genome primers. The volume and concentrations for template DNA, primers, and reaction buffer are listed below.

TABLE 2 qPCR Components.

| Reagent | Concentration per Reaction | Volume per Reaction |
|---|---|---|
| Reaction Buffer | 1X | 12.5 µl |
| Primer (forward and reverse) | 250 nM | 0.0625 µl of each 100 umole stock |
| ddH$_2$O | N/A | 2.375 µl |
| Template DNA | 20 ng | 10.0 µl |
| Total | | 25 µl |

The cycling parameters for each amplicon are listed in Table 3.

TABLE 3

Cycling Parameters.

| Step | Temperature (° C.) | Duration |
|---|---|---|
| 1 | 95 | 3 min |
| 2 | 95 | 30 sec |
| 3 | 66 (3.4 deletion primers) or 61.5 (12 s primers) or 61.5 (TNF primers) | 30 sec |
| 4 | 72 | 30 sec |
| 5 | Plate Read | |
| 6 | 72 | 10 min |
| 7 | Melting Curve 50° C.-110° C. reading every 1° C. | 3 sec |

Repeat steps 2-5, 44 times for a total of 45 cycles.

Thermal cycling, real-time detection and analysis of the reactions was carried out using a DNA Engine Opticon® 2 Continuous Fluorescence Detection System equipped with Intuitive Opticon Monitor™ software (MJ Research Inc.). The standard curve method was utilized for DNA quantification. A set of serial dilutions ($10^6$, $10^5$, $10^4$, $10^3$, $10^2$, $10^1$) of three purified PCR generated templates, one product for the 3.4 deletion, one for the 12s primers, and one for TNF. From this, three different standard curves were generated showing the number of copies of total mtDNA (12s amplicon-total mitochondrial genome primers), the amount of mtDNA having the 3.4 kb deletion, or total nuclear DNA (TNF-single copy nuclear gene primers). The $C_T$ values of the samples were then converted to the number of DNA copies by comparing the sample $C_T$ to that of the standards. The 3.4 deletion was considered to be absent or at low levels if the deletion was not detected within 37 cycles.

The determination of malignancy is based upon the quantity of the 3.4 kb deletion present in the normalized sample as indicated by the location of the cycle threshold. This location may be either absolute, as in greater than 25 cycles but less than 35 cycles, or more likely a ratio between the total mitochondrial DNA as indicated by the 12s amplicon, and the 3.4 kb deletion. This may be expressed as a percent of the total mitochondrial DNA. The number of cells, as represented by the TNF amplicon, may be incorporated to refine the distinction between benign and malignant tissues.

In order to automate the analyses of these samples, bioinformatics tools were employed. The three variables that were considered for these analyses were the cycle threshold $C_T$ of Tumour Necrosis Factor (TNF), total pieces of mitochondria that contain those specific primer sites, and those mitochondria that harbour the deletion of interest.

Cluster Analysis

The clustering was not normalized nor were logarithmic functions used due to the similar and small range of data.

Figure 3:
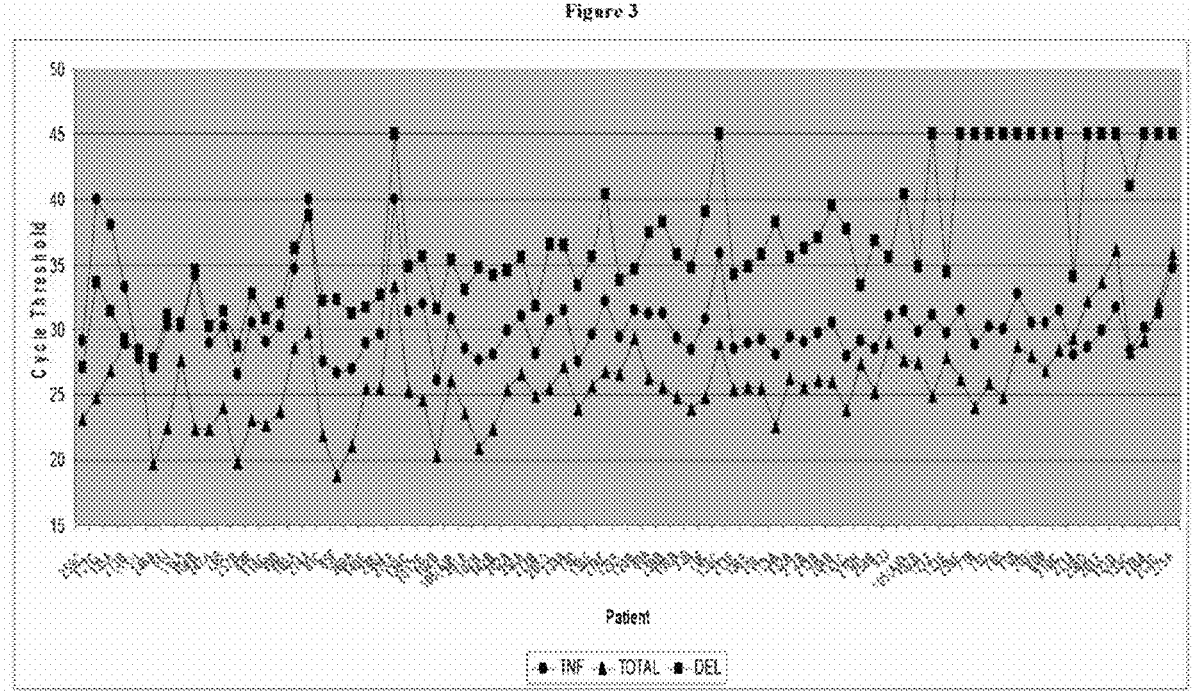
FIG. 3 is a graph showing cycle threshold as related to Example 1.
Figure 4:
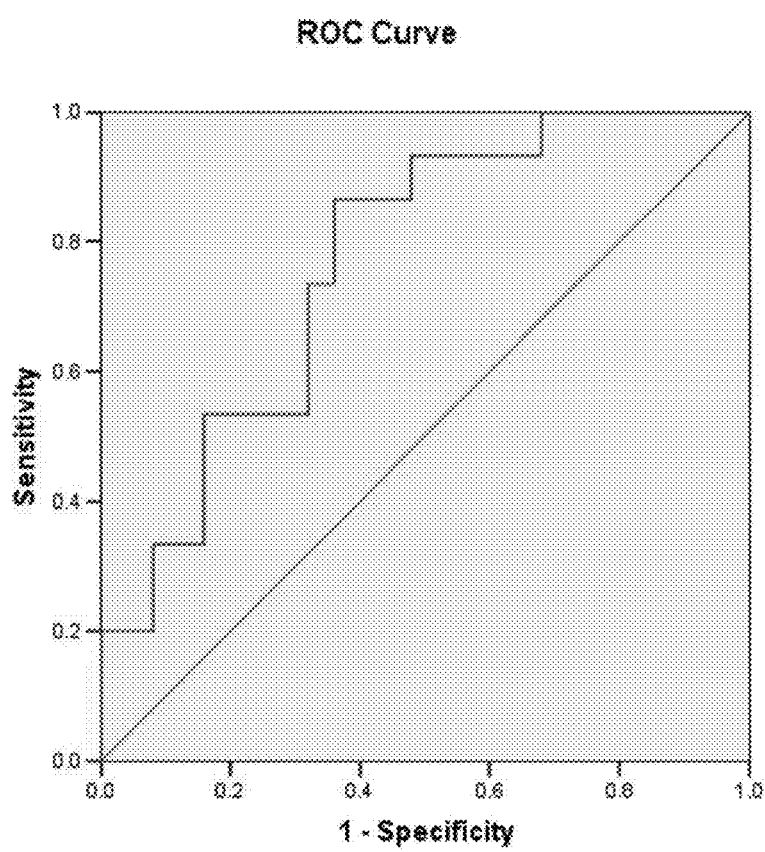
FIG. 4 shows a ROC curve illustrating the specificity and sensitivity of one embodiment of the present invention.

FIG. 3 shows the actual movement and trends of the data. The x-axis is the patient number and the y-axis is the cycle threshold obtained from real time PCR.

It is important to note that the higher the cycle threshold is, the lower amount of the deletion is present.

The general trend shown in FIG. 3 is based upon the differences/ratios between the variables of Deletion, Total, and TNF. The deletion is low to absent for the benign/normal samples (right side) and increases (toward the left) with abnormal benign and malignant samples. The abnormal benign and malignant samples begin to differentiate themselves from each other based on the cycle threshold ratio of Deletion to TNF.

Supervised Learning

Supervised learning is based on the system trying to predict outcomes for known samples. Half of the data was used to train and the other half to test the algorithm. Supervised learning compares its predictions to the target answer and "learns" from its mistakes. But, if the predicted output is higher or lower than the actual outcome in the data, the error is propagated back through the system and the weights are adjusted accordingly.

Data SET:

5% to 35%—Benign

35% to 65%—Hyperplasia

65% to 95%—Malignant

Figure 8:
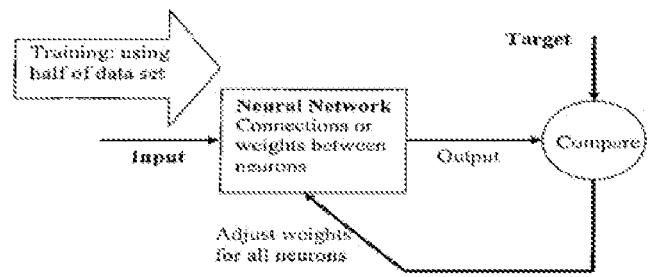
FIG. 8 schematically illustrates an Artificial Neural Network (ANN) Algorithm according to an aspect of the invention.

An Artificial Neural Network (ANN) Algorithm is shown in FIG. 8, wherein:

Half of Data set used for Training ANN

Other half used to compare the accuracyAccuracy=Compare expected data set with obtained data set→86.6%.

Supervised Learning of Deletion Data using Artificial Neural Network (ANN)

Three Classifications:

Benign

Hyperplasia

Malignant

Three variables for each classification were used based on Real Time PCR Cycle Threshold $C_T$:

Tumour Necrosis Factor (TNF)—Nuclear copy control.

Total Mitochondria—Mitochondria copy control

Deletion—Mitochondria in the deleted state.

Results:

Half of data set is used to train the ANN, and the remaining half is used to compare the accuracy.

Three Classification Accuracy=86.6%

Positive Predictive Value (PPV);

Benign to Malignant=88.2%

Negative Predictive Value (NPV)

Benign to Malignant=76.5%

EXAMPLE 4

3.4 kb Deletion in mtDNA Associated with Breast Cancer 18 samples were tested from malignant and benign breast tissue, 9 being malignant and 9 being benign, for the presence of the aforementioned 3.4 kb deletion. Samples were classified as either malignant or benign using conventional histopathological analysis.

DNA was isolated and purified from the samples using a QIAamp® DNA Mini Kit (Qiagen, Cat. #51304) according to manufacturer's specifications.

Purified oligonucleotide primers were chemically synthesized by Invitrogen (California, USA). The sequences of the primers and the expected sizes of the PCR products amplified are listed in Table 1 above.

Real-Time Polymerase Chain Reaction

Three separate PCRs were performed on each sample. Each reaction was 25 µl total volume and included template DNA, one pair of primers (12s or 3.4 Deletion or TNF), an iQ™ SYBR Green Supermix kit (Catalogue Number 170-8882, Bio-Rad Laboratories Inc.) and distilled deionized water (ddH$_2$O). The TNF (tumor necrosis factor) comprised single copy nuclear gene primers, and 12s comprised total mitochondrial genome primers. The volume and concentrations for template DNA, primers, and reaction buffer are listed below:

TABLE 4 qPCR Components.

| Reagent | Concentration per Reaction | Volume per Reaction |
| --- | --- | --- |
| Reaction Buffer | 1X | 12.5 µl |
| Primer (forward and reverse) | 250 nM | 0.0625 µl of each 100 µmole stock |
| ddH$_2$O | N/A | 2.375 µl |
| Template DNA | 20 ng | 10.0 µl |
| Total | | 25 µl |

The cycling parameters for each amplicon are listed in Table 5.

TABLE 5

Cycling Parameters.

| Step | Temperature (° C.) | Duration |
| --- | --- | --- |
| 1 | 95 | 3 min |
| 2 | 95 | 30 sec |
| 3 | 66 (3.4 deletion primers) or 61.5 (12 s primers) or 61.5 (TNF primers) | 30 sec |
| 4 | 72 | 30 sec |
| 5 | Plate Read | |
| 6 | 72 | 10 min |
| 7 | Melting Curve 50° C.-110° C. reading every 1° C. | 3 sec |

Repeat steps 2-5, 44 times for a total of 45 cycles.

Thermal cycling, real-time detection and analysis of the reactions was carried out using a DNA Engine Opticon® 2 Continuous Fluorescence Detection System equipped with Intuitive Opticon Monitor™ software (MJ Research Inc.). The standard curve method was utilized for DNA quantification. A set of serial dilutions ($10^6$, $10^5$, $10^4$, $10^3$, $10^2$, 10') of three purified PCR generated templates were performed, one product for the 3.4 deletion, one for the 12s primers, and one for TNF. From this, three different standard curves were generated showing the number of copies of total mtDNA (12s amplicon-total mitochondrial genome primers), 3.4 deletion or total nuclear DNA (TNF-single copy nuclear gene primers). The $C_T$ values of the samples were then converted to the number of DNA copies by comparing the sample $C_T$ to that of the standards.

The determination of malignancy was based upon the quantity of the 3.4 kb deletion present in the normalized sample as indicated by the location of the cycle threshold. This location may be either absolute, as in greater than 25 cycles but less than 30 cycles, or more likely a ratio between the total mitochondrial DNA present as indicated by the 12s amplicon, and the 3.4 kb deletion. This may be expressed as a percent of the total mitochondrial DNA.

In order to automate the analyses of these samples, bioinformatics tools were employed. The three variables that were considered for these analyses were the cycle threshold $C_T$ of Tumour Necrosis Factor (TNF), total species of mitochondria that contain those specific primer sites, and those mitochondria that harbour the deletion of interest.

Figure 7:
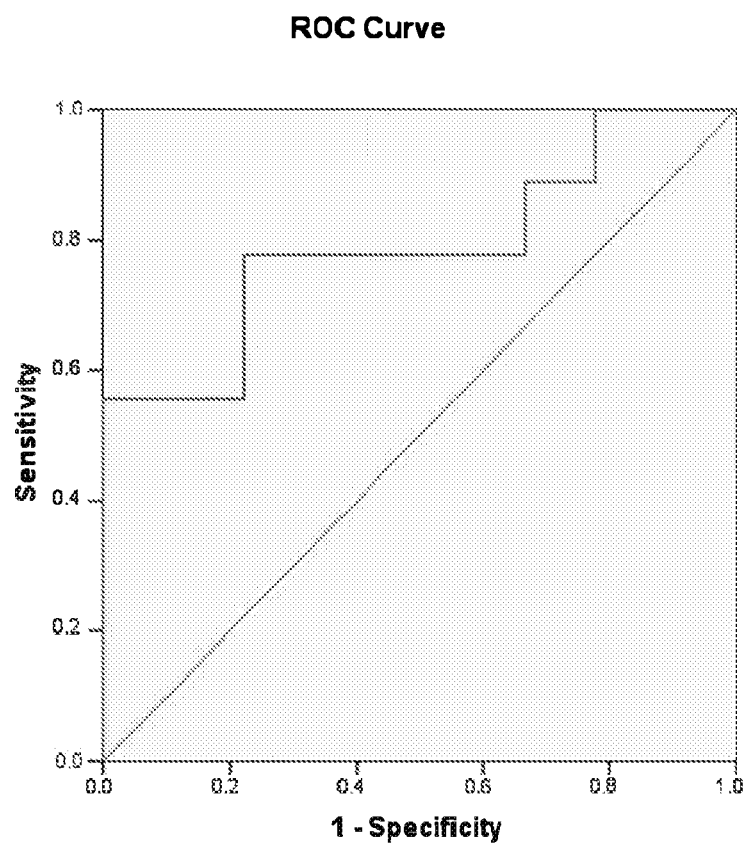

Table 6 and FIG. 7 show the difference in the mean $C_T$ scores for samples from malignant tissue and benign tissue. The mean $C_T$ value for normal tissue was 30.5889, while the mean $C_T$ for malignant tissue was 27.8533 thereby illustrating a difference in the quantity of mtDNA having the 3.4 kb deletion in malignant breast tissue compared to normal breast tissue.

TABLE 6

Mean values for $C_T$ scores
Group Statistics

| | GRP | N | Mean | Std. Deviation | Std. Error Mean |
|---|---|---|---|---|---|
| del3.4 | normal | 9 | 30.5889 | 2.53897 | .84632 |
| | malignant | 9 | 27.8533 | 2.52253 | .84084 |

FIG. 8 is an ROC curve illustrating the specificity and sensitivity of the 3.4 kb mtDNA deletion as a marker for breast cancer when testing breast tissue. These results were obtained using a cutoff $C_T$ of 29.1900. The sensitivity of the marker at this $C_T$ was 77.8%, while the specificity was 77.8%.

Table 7 shows the calculation of the area under the curve for the present example. As a measure of the accuracy of the test.

TABLE 7

Results Showing Area Under the Curve
Area Under the Curve
Test Result Variable(s): del3.4

| Area | Std. Error[a] | Asymptotic Sig.[b] | Asymptotic 95% Confidence Interval | |
|---|---|---|---|---|
| | | | Lower Bound | Upper Bound |
| .790 | .112 | .038 | .570 | 1.010 |

[a]Under the nonparametric assumption
[b]Null hypothesis: true area = 0.5

The determination of the cutoff $C_T$ of 29.1900 is shown in table 8 below. The results listed in table 8 show that a cutoff $C_T$ of 29.1900 provided the highest sensitivity and specificity at 78% and 78% respectively.

TABLE 8

Determination of $C_T$ cutoff.
Coordinates of the Curve
Test Result Variable(s): del3.4

| Positive if Less Than or Equal To[a] | Sensitivity | 1 − Specificity |
|---|---|---|
| 24.6000 | .000 | .000 |
| 25.6800 | .111 | .000 |
| 25.7700 | .222 | .000 |
| 25.9250 | .333 | .000 |
| 26.2050 | .444 | .000 |
| 26.8400 | .556 | .000 |
| 27.4800 | .556 | .111 |
| 28.1600 | .556 | .222 |
| 28.8800 | .667 | .222 |
| 29.1900 | .778 | .222 |
| 29.4600 | .778 | .333 |
| 29.8750 | .778 | .444 |
| 30.5850 | .778 | .556 |
| 31.2200 | .778 | .667 |
| 31.5000 | .889 | .667 |
| 31.7650 | .889 | .778 |
| 32.9900 | 1.000 | .778 |
| 34.3350 | 1.000 | .889 |
| 35.6400 | 1.000 | 1.000 |

[a]The smallest cutoff value is the minimum observed test value minus 1, and the largest cutoff value is the maximum observed test value plus 1. All the other cutoff values are the averages of two consecutive ordered observed test values.

EXAMPLE 5

The 3.4 kb Deletion in the Prostate Massage Fluid of Individuals with Prostate Cancer as Compared to the Fluid from Those Without Histological Evidence of Prostate Cancer Forty prostate massage fluid samples were collected by urologists from patients who were either subsequently diagnosed with prostate cancer or showed no histological evidence of prostate cancer following a prostate needle biopsy procedure. The sample was deposited on a IsoCode Card™ (Schleicher & Shuell), dried, and then extracted according to the manufacturer's protocol. All DNA extracts were quantified using a NanoDrop™ ND-1000 Spectrophotometer and the DNA concentration normalized to 2 ng/ul. Each sample was then amplified according to the following parameters:

```
1X iQ SYBR Green Supermix ™ (Bio-Rad P/N 170-8880)
150 nmol forward primer
                                            (SEQ ID NO: 2)
(5'-TAGACTACGTACATACTAACCCTACTCCTA-3').

150 nmol reverse primer
                                            (SEQ ID NO: 3)
(5'-GAGGTAGGATTGGTGCTGT-3')

20 ng template DNA in a 25 ul reaction.
```

Reactions were cycled on an Opticon™ 2 DNA Engine (Bio-Rad Canada) according to the following protocol:
1. 95° C. for 3 minutes
2. 95° C. for 30 seconds
3. 66° C. for 30 seconds
4. 72° C. for 30 seconds
5. Plate Read
6. Repeat steps 2-5 44 times
7. 72° C. for 10 minutes
8. Melting Curve from 50° C. to 105° C., read every 1° C., hold for 3 seconds
9. 10° C. Hold

TABLE 9

Results showing the mean $C_T$ Values for Prostate Massage Fluid Test
Group Statistics

| Group | | N | Mean | Std. Deviation | Std. Error Mean |
|---|---|---|---|---|---|
| DEL3.4 | benign | 25 | 37.1869 | 3.18495 | .63699 |
| | malignant | 15 | 33.7712 | 3.98056 | 1.02778 |

Tables 9 and 10 show a significant difference between the mean $C_T$ values obtained for the benign sample and the malignant sample groups (p=0.005).

TABLE 10

Results Showing Difference (p = 0.005) for $C_T$ values of samples.
Independent Samples Test

| | | Levene's Test for Equality of Variances | | t-test for Equality of Means | | | | | | 95% Confidence Interval of the Difference | |
|---|---|---|---|---|---|---|---|---|---|---|---|
| | | F | Sig. | t | of | Sig. (2-tailed) | Mean Difference | std. Error Difference | | Lower | Upper |
| DEL34 | Equal Variances assumed | 1.251 | .270 | 2989 | 38 | .005 | 341570 | 1.14283 | | 1.10217 | 5.72923 |
| | Equal Variances not assumed | | | 2825 | 24.696 | .009 | 341570 | 1.20917 | | .92382 | 5.90758 |

Figure 5:
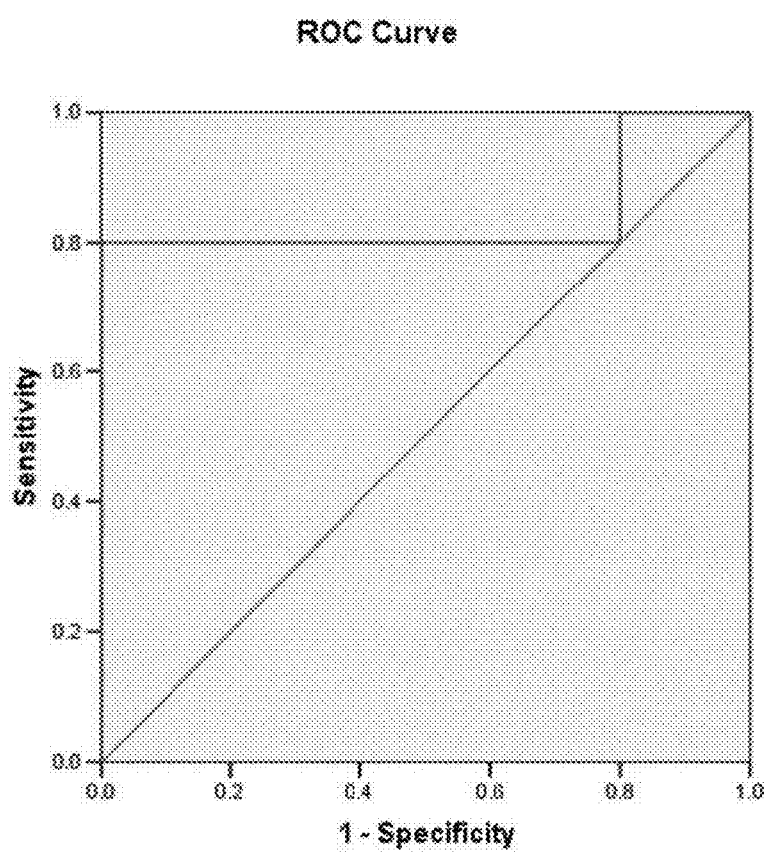
FIG. 5 shows a ROC curve illustrating the specificity and sensitivity of another embodiment of the present invention.

FIG. 5 is a Receiver Operating Characteristic (ROC) curve illustrating the specificity and sensitivity of the 3.4 kb mtDNA deletion as a marker for prostate cancer when testing prostate massage fluid. These results were obtained using a cutoff $C_T$ of 37.3683. The sensitivity of the marker at this $C_T$ is 87%, while the specificity is 64%.

The accuracy of the test depends on how well the test separates the group being tested into those with and without the prostate cancer. Accuracy is measured by the area under the ROC curve. Table 11 shows the calculation of the area under the curve for the present example.

TABLE 11

Results Showing Area Under the ROC Curve
Area Under the Curve
Test Result Variable(s): DEL3.4

| Area | Std. Error[a] | Asymptotic Sig.[b] | Asymptotic 95% Confidence Interval | |
|---|---|---|---|---|
| | | | Lower Bound | Upper Bound |
| .768 | .074 | .005 | .622 | .914 |

[a]Under the nonparametric assumption
[b]Null hypothesis: true area = 0.5

TABLE 12

Determination of Specificity and Sensitivity
Coordinates of the Curve
Test Result Variable(s): DEL3.4

| Positive if Less Than or Equal To[a] | Sensitivity | 1 − Specificity |
|---|---|---|
| 26.2992 | .000 | .000 |
| 27.3786 | .067 | .000 |
| 28.2484 | .133 | .000 |
| 29.5193 | .200 | .000 |
| 30.1757 | .200 | .040 |
| 30.4580 | .200 | .080 |
| 30.5980 | .267 | .080 |
| 31.5709 | .333 | .080 |
| 32.5712 | .333 | .120 |
| 32.9500 | .333 | .160 |
| 33.3314 | .400 | .160 |
| 33.6547 | .467 | .160 |
| 33.9247 | .533 | .160 |
| 34.3554 | .533 | .200 |
| 34.9056 | .533 | .240 |
| 35.4650 | .533 | .280 |
| 35.9172 | .533 | .320 |
| 36.0648 | .600 | .320 |
| 36.3616 | .667 | .320 |
| 36.6421 | .733 | .320 |

TABLE 12-continued

Determination of Specificity and Sensitivity
Coordinates of the Curve
Test Result Variable(s): DEL3.4

| Positive if Less Than or Equal To[a] | Sensitivity | 1 − Specificity |
|---|---|---|
| 36.8531 | .733 | .360 |
| 37.1188 | .800 | .360 |
| 37.3883 | .867 | .360 |
| 37.5200 | .867 | .400 |
| 37.8341 | .867 | .440 |
| 38.2533 | .867 | .480 |
| 38.5198 | .933 | .480 |
| 38.6519 | .933 | .520 |
| 38.8552 | .933 | .560 |
| 39.1258 | .933 | .600 |
| 39.2734 | .933 | .640 |
| 39.4952 | .933 | .680 |
| 39.7323 | 1.000 | .680 |
| 39.8956 | 1.000 | .720 |
| 41.0000 | 1.000 | 1.000 |

The smallest cutoff value is the minimum observed test value −1, and the largest cutoff value is the maximum observed test value plus 1. All the other cutoff values are the average of two consecutive ordered, observed test values.

The determination of the cutoff $C_T$ of 37.3683 is shown in table 12 above. The results listed in table 12 illustrate that a cutoff $C_T$ of 37.3683 provided the highest sensitivity and specificity.

EXAMPLE 6

The 3.4 kb Deletion in the Urine of Individuals with Prostate Cancer as Compared to the Fluid From Those Without Histological Evidence of Prostate Cancer Urine samples were collected from 5 patients who were diagnosed with prostate cancer and 5 who have had a needle biopsy procedure which was unable to detect prostate malignancy. These samples were collected following a digital rectal exam (DRE) to facilitate the collection of prostate cells.

Upon receipt of the samples a 5 ml aliquot was removed and then 2 mls were centrifuged at 14,000×g to form a pellet. The supernatant was removed and discarded. Pellets were resuspended in 200 μl phosphate buffered saline solution. Both the resuspended pellet and the whole urine sample were subjected to a DNA extraction procedure using the QiaAMP™ DNA Mini Kit (Qiagen P/N 51304) according to the manufacturer's directions. The resulting DNA extracts were then quantified using a NanoDrop™ ND-1000 Spectrophotometer and normalized to a concentration of 0.1 ng/ul.

Samples were analyzed by quantitative real-time PCR with the 3.4 kb deletion specific primers according to the following:

```
1X iQ SYBR Green Supermix ™ (Bio-Rad P/N 170-8880)
100 nmol forward primer
                                        (SEQ ID NO: 2)
(5'-TAGACTACGTACATACTAACCCTACTCCTA-3')

100 nmol reverse primer
                                        (SEQ ID NO: 3)
(5'-GAGGTAGGATTGGTGCTGT-3')

1 ng template DNA in a 25 ul reaction.
```

Reactions were cycled on an Opticon™2 DNA Engine (Bio-Rad Canada) according to the following protocol:
1. 95° C. for 3 minutes
2. 95° C. for 30 seconds
3. 69° C. for 30 seconds
4. 72° C. for 30 seconds
5. Plate Read
6. Repeat steps 2-5 44 times
7. 72° C. for 10 minutes
8. Melting Curve from 50° C. to 105° C., read every 1° C., hold for 3 seconds
9. 10° C. Hold

| Group Statistics | | | | |
|---|---|---|---|---|
| GRPfluid38 | N | Mean | Std. Deviation | Std. Error Mean |
| CTf Benign | 5 | 33.2780 | 1.10900 | .49596 |
| Malignant | 5 | 30.6980 | 2.55767 | 1.14382 |

Tables 13 and 14 show a significant difference between the mean $C_T$ values obtained for benign sample and the malignant sample groups (p=0.005).

TABLE 14

Results Showing Difference (p = 0.005) for $C_T$ values of samples.
Independent Samples Test

| | | Levene's Test for Equality of Variances | | t-test for Equality of Means | | | | | 95% Confidence Interval of the Difference | |
|---|---|---|---|---|---|---|---|---|---|---|
| | | F | Sig. | t | of | Sig. (2-tailed) | Mean Difference | std. Error Difference | Lower | Upper |
| CTf | Equal Variances assumed | 1272 | .292 | 2069 | 8 | .072 | 258000 | 1.24672 | −.29494 | 545494 |
| | Equal Variances not assumed | | | 2069 | 5453 | .089 | 258000 | 1.24672 | −.54639 | 570639 |

TABLE 15

Determination of $C_T$ cutoff.
Coordinates of the Curve
Test Result Variable(s): CTf

| Positive if Less Than or Equal To[a] | Sensitivity | 1 − Specificity |
|---|---|---|
| 26.2900 | .000 | .000 |
| 28.4950 | .200 | .000 |
| 30.3850 | .400 | .000 |
| 31.0800 | .600 | .000 |
| 31.5750 | .800 | .000 |
| 32.1400 | .800 | .200 |
| 32.8150 | .800 | .400 |
| 33.8700 | .800 | .600 |
| 34.3350 | .800 | .800 |
| 34.3550 | 1.000 | .800 |
| 35.3700 | 1.000 | 1.000 |

[a]The smallest cutoff value is the minimum observed test value minus 1, and the largest cutoff value is the maximum observed test value plus 1. All the other cutoff values are the averages of two consecutive ordered observed test values.

EXAMPLE 7

Detection of Re-Circularized 3.4 kb Deleted Sequence in Prostate Malignant and Benign Tissue In this example, the amount of re-circularized 3.4 kb deleted mtDNA molecules in samples was tested as an indicator for prostate cancer. As mentioned above, the 3.4 kb sequence, upon deletion, may reform as a circular mtDNA molecule. Amplification of a target region from the deleted 3.4 kb mtDNA sublimon was conducted using a primer pair (SEQ ID NOS: 9 and 10). The forward primer (SEQ ID NO: 9), overlaps the rejoining site of the ends of the 3.4 kb sequence.

Prostate tissue was formalin-fixed paraffin embedded prostate tissue needle biopsies.

The reagent setup used for this example was as follows:
250 nmol each primer
12.5 ul of 2x reaction mix,
20 ng (10 ul of 2 ng/ul) template in 25 ul reaction volume.

Figure 6:
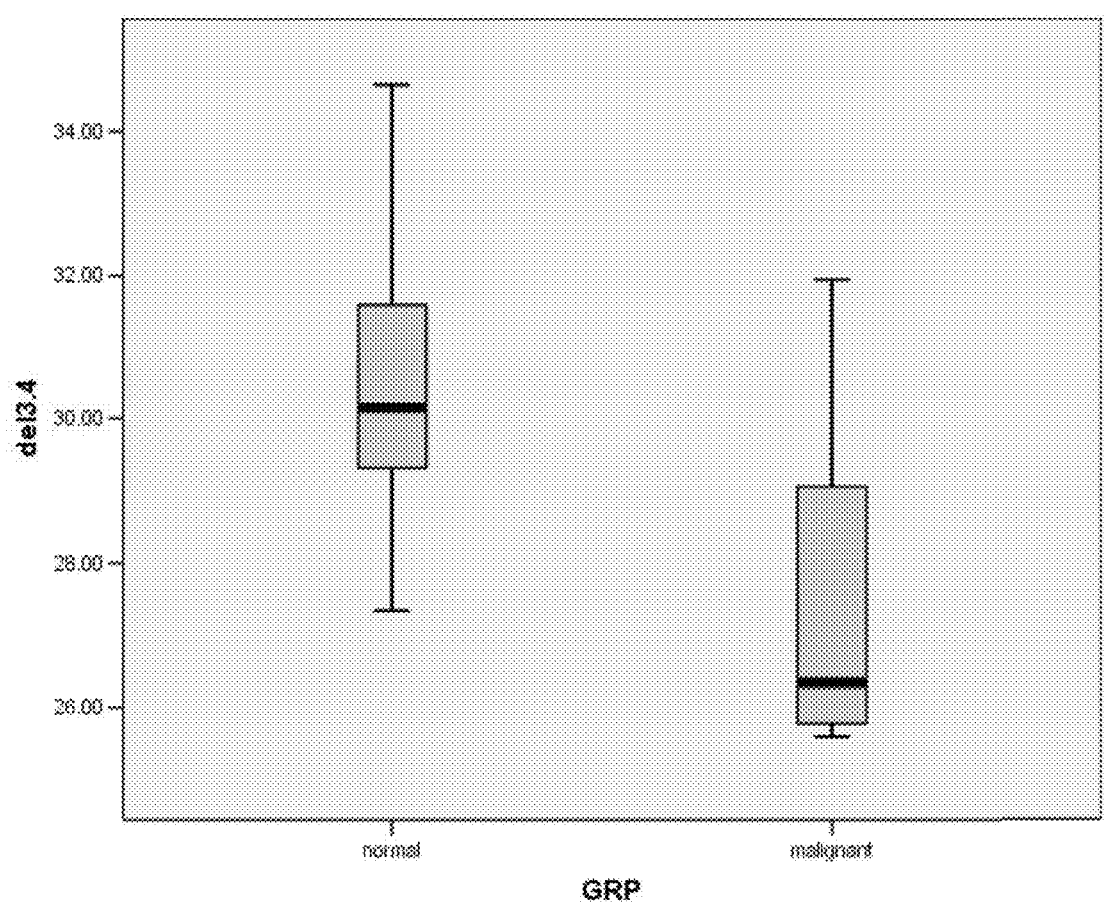
FIG. 6 shows real-time PCR data relating to 3.4 kb mtDNA deletion levels associated with breast cancer; and, FIG. 7 shows a ROC curve illustrating the specificity and sensitivity of another embodiment of the present invention.

FIG. 6 is a Receiver Operating Characteristic (ROC) curve illustrating the specificity and sensitivity of the 3.4 kb mtDNA deletion as a marker for prostate cancer when testing urine. These results were obtained using a cutoff $C_T$ of 31.575. The sensitivity of the marker at this $C_T$ is 80%, while the specificity is 100%.

The determination of the cutoff $C_T$ of 31.575 is shown in table 15. The results listed in table 15 show that a cutoff $C_T$ of 31.575 provided the highest sensitivity and specificity.

The cycling parameters were as follows:
1. 95 degrees Celsius for 3 minutes
2. 95 degrees Celsius for 30 seconds
3. 62 degrees Celsius for 30 seconds
4. 72 degrees Celsius for 30 seconds
5. Plate Read
6. Repeat steps 2-5 44 times
7. 72 degrees for 10 minutes 8. Melting Curve from 50-100 degrees, reading every 1 degree for 3 seconds
9 4 degrees HOLD.

Amplification of a target region from the deleted 3.4 kb mtDNA sublimon was conducted using a primer pair (SEQ ID NOS: 9 and 10).

Table 16 below provides a summary of testing conducted for the detection of the actual 3.4 kb deleted in mtDNA obtained from malignant and benign prostate tissue. Using a $C_T$ score of 30.0, a clear identification of malignant and benign tissue was possible. As such, an increase in the amount of the 3.4 kb molecule present in a sample was indicative of cancer.

TABLE 16

$C_T$ scores for Detection of Cancer in Prostate Tissue

| Description | $C_T$ |
| --- | --- |
| Benign sample 1 | 33.75 |
| Malignant sample 1 | 28.79 |
| Benign sample 2 | 30.96 |
| Malignant sample 2 | 28.4 |
| Benign sample 3 | 32.19 |
| Malignant sample 3 | 27.38 |

Although the invention has been described with reference to certain specific embodiments, various modifications thereof will be apparent to those skilled in the art without departing from the spirit and scope of the invention as outlined in the claims appended hereto.

REFERENCES

Birch-Machin M A, Online Conference Report (Sunburnt DNA), International Congress of Biochemistry and Molecular Biology, New Scientist, 2000(a)

Birch-Machin M A, Taylor R W, Cochran B, Ackrell B A C, Turnbull D M. Ann Neurol 48: 330-335, 2000(b)

Birch-Machin, M. A. (2000). Mitochondria and skin disease. Clin Exp Dermatol, 25, 141-6.

Brown, M. D., et al., Am J. Humn Genet, 60: 381-387, 1997

Bogliolo, M, et al., Mutagenesis, 14: 77-82, 1999

Chinnery P F and Turnbull D M., Lancet 354 (supplement 1): 17-21, 1999

Huoponen, Kirsi, Leber hereditary optic neuropathy: clinical and molecular genetic findings, Neurogenetics (2001) 3: 119-125.

Hayward S W, Grossfeld G D, Tlsty T D, Cunha G R., Int J Oncol 13:35-47, 1998

Huang G M, Ng W L, Farkas J, He L, Liang H A, Gordon D, Hood R., Genomics 59(2):178-86, 1999

Konishi N, Cho M, Yamamoto K, Hiasa Y. Pathol. Int. 47:735-747, 1997

Landis S H, Murray T, Bolden S, Wingo P A. Cancer J Clin. 49:8-31

Lee H C, Lu C Y, Fahn H J, Wei Y Hu. Federation of European Biochemical Societies, 441:292-296, 1998

Mitochondrial Research Society http://www.mitoresearch.org/diseases.html.

MITOMAP: A human mt genome database (www.gen.emory.edu/mitomap.html)

Naviaux, R K., Mitochondrial Disease—Primary Care Physician's Guide. Psy-Ed. Corp D/B/A Exceptional Parents Guide: 3-10, 1997

Parrella P, Xiao Y, Fliss M, Sanchez-Cespedes M, Mazzarelli P, Rinaldi M, Nicol T, Gabrielson E, Cuomo C, Cohen D, Pandit S, Spencer M, Rabitti C, Fazio V M, Sidransky D: Detection of mitochondrial DNA mutations in primary breast cancer and fine-needle aspirates. Cancer Res 2001, 61:7623-7626

Polyak Y, et al., Nature Genet. 20 (3):291-293, 1998

Seidman, M. D. et al., Arch. Otolaryngol Head Neck Surg., 123: 1039-1045, 1997

Sherrat E J, Thomas A W, Alcolado J C., Clin. Sci. 92:225-235, 1997

Shoffner J M, Brown M D, Torroni A, Lott M T, Cabell M F, Mirra S S, Beal M F, Yang C, Gearing M, Salvo R, Watts R L, Juncos J L, Hansen L A, Crain B J, Fayad M, Reckford C L, and Wallace D C., Genomics 17: 171-184, 1993

SpringNet—CE Connection: Screening, Diagnosis: Improving Primary Care Outcomes. Website: http://www.springnet.com/ce/j803a.htm Taniike, M. et al., BioChem BioPhys Res Comun, 186: 47-53, 1992

Valnot, Isabelle, et al., A mitochondrial cytochrome b mutation but no mutations of nuclearly encoded subunits in ubiquinol cytochrome c reductase (complex III) deficiency, Human Genetics (1999) 104: 460-466 von Wurmb, N, Oehmichen, M, Meissner, C., Mutat Res. 422:247-254, 1998

Wallace et al., Mitochondiral DNA MUtatio Associated with Leber's Hereditary Optic Neuropathy, Science, 1427-1429

Wei Y H. Proceedings of the Nat. Sci. Council of the Republic of China April 22(2):5567, 1998

Woodwell D A. National Ambulatory Medical Care Survey: 1997 Summary. Advance data from vital and health statistics; no. 305. Hyattsville, Md.: National Center for Health Statistics. 1999

Yeh, J. J., et al., Oncogene Journal, 19: 2060-2066, 2000

Zhang et al., Multiple mitochondrial DNA deletions in an elderly human individual, FEBS Lett, 297, 34-38 1992

Zhang, C., et al., BioChem. BioPhys. Res. Comun., 195: 1104-1110, 1993

What we claim is:

1. A method of detecting a cancer in an individual comprising;
   a) extracting mitochondrial DNA, mtDNA, from a biological sample from the individual;
   b) quantifying the amount of a mtDNA deletion in the sample, the deletion having a nucleic acid sequence as set forth in SEQ ID NO: 1, the step of quantifying comprising the use of a pair of amplification primers, wherein one of the pair of amplification primers is adapted to bind to a rejoining site of the deletion after the deletion has re-circularized;
   c) comparing the amount of the deletion in the sample to at least one known reference value.

2. The method of claim 1, wherein the at least one known reference value is the amount of the deletion in a reference sample of mtDNA from known non-cancerous tissue or body fluid.

3. The method of claim 1, wherein the at least one known reference value is the amount of the deletion in a reference sample of mtDNA from known cancerous tissue or body fluid.

4. The method of claim 1, wherein the step of quantifying is conducted using real-time PCR.

5. The method of claim 4, wherein the one of the pair of amplification primers has a nucleic acid sequence as set forth in SEQ ID NO: 9.

6. The method of claim 1, wherein the one of the pair of amplification primers has a nucleic acid sequence as set forth in SEQ ID NO: 9.

7. The method of claim 1, wherein the cancer is prostate cancer.

8. The method of claim 1, wherein the cancer is breast cancer.

9. The method of claim 1, wherein the biological sample is a body tissue or a body fluid.

10. The method of claim 1, wherein the biological sample is breast tissue, prostate tissue, prostate massage fluid, or urine.

11. The method of claim 4, wherein the reference value is a cycle threshold.

12. A method of monitoring an individual for the development of a cancer, the method comprising:
   a) extracting mitochondrial DNA, mtDNA, from a biological sample obtained from the individual at a first time point;
   b) quantifying the amount of a mtDNA deletion in the sample, the deletion having a nucleic acid sequence as set forth in SEQ ID NO: 1, the step of quantifying comprising the use of a pair of amplification primers, wherein one of the pair of amplification primers is adapted to bind to a rejoining site of the deletion after the deletion has re-circularized;
   c) repeating steps a) to b) at one or more second time points;
   wherein an increasing level of the deletion over time is indicative of the presence or development of the cancer.

13. The method of claim 12 further comprising: (i) comparing the amount of the deletion in the sample to the amount of the deletion in a reference sample of mtDNA from known non-cancerous tissue or body fluid; and/or (ii) comparing the amount of the deletion in the sample to the amount of the deletion in a reference sample of mtDNA from known cancerous tissue or body fluid.

14. The method of claim 12, wherein the step of quantifying is conducted using real-time PCR.

15. The method of claim 12, wherein the one of the pair of amplification primers has the nucleic acid sequence set forth in SEQ ID NO: 9.

16. The method of claim 12, wherein the cancer is prostate cancer.

17. The method of claim 12, wherein the cancer is breast cancer.

18. The method of claim 12, wherein the biological sample is a body tissue or a body fluid.

19. The method of claim 12, wherein the biological sample is breast tissue, prostate tissue, prostate massage fluid, or urine.

20. A kit for detecting a cancer in a subject, the kit comprising a pair of PCR primers for amplifying a target region of mitochondrial DNA, mtDNA, in a biological sample obtained from the subject, said target region comprising a region of the mtDNA having a deletion spanning approximately nucleotides 10744 and 14124 of the mtDNA genome.

21. The kit of claim 20, wherein one primer of the pair of primers is adapted to bind to a region of the mtDNA comprising a splice joining opposite ends of the mtDNA sequence after removal of the deletion.

22. The kit of claim 20, wherein one primer of the pair of primers has a nucleic acid sequence as set forth in SEQ ID NO: 2.

23. The kit of claim 20, wherein the cancer is breast cancer or prostate cancer.

24. The kit of claim 20, further comprising reagents and/or instructions.

25. A kit for detecting a cancer in a subject, the kit comprising a pair of PCR primers for amplifying a mitochondrial DNA, mtDNA, deletion in a biological sample obtained from the subject, said deletion having a nucleic acid sequence as set forth in SEQ ID NO: 1, wherein one primer of the pair of primers is adapted to bind to a region of the deletion comprising a rejoining site of the deletion after the deletion has re-circularized.

26. The kit of claim 25, wherein the one primer of the pair of primers has a nucleic acid sequence as set forth in SEQ ID NO: 2.

27. The kit of claim 25, wherein the cancer is breast cancer or prostate cancer.

28. The kit of claim 25, further comprising reagents and/or instructions.

* * * * *